US012000855B2

(12) United States Patent
Alloush et al.

(10) Patent No.: US 12,000,855 B2
(45) Date of Patent: Jun. 4, 2024

(54) AUTOMATED APPARATUS FOR CHARACTERIZATION OF FLUID-SOLID SYSTEMS

(71) Applicant: UNIVERSITY OF WYOMING, Laramie, WY (US)

(72) Inventors: Rami Alloush, Laramie, WY (US); Mohammad Piri, Laramie, WY (US); Evan W. Lowry, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 0 days.

(21) Appl. No.: 17/740,488

(22) Filed: May 10, 2022

(65) Prior Publication Data

US 2022/0357256 A1   Nov. 10, 2022

Related U.S. Application Data

(60) Provisional application No. 63/186,366, filed on May 10, 2021.

(51) Int. Cl.
*G01N 5/02* (2006.01)
*G01N 1/44* (2006.01)
(Continued)

(52) U.S. Cl.
CPC .............. *G01N 5/02* (2013.01); *G01N 1/44* (2013.01); *G01N 33/24* (2013.01); *G01N 30/06* (2013.01)

(58) Field of Classification Search
CPC ............ G01N 5/02; G01N 1/44; G01N 33/24; G01N 30/06; G01N 15/0806; G01N 15/082

See application file for complete search history.

(56) References Cited

U.S. PATENT DOCUMENTS 10,302,540 B2   5/2019   Piri et al.
11,340,208 B2 *  5/2022   Pujol ................... G01N 33/246
(Continued)

OTHER PUBLICATIONS

Barsotti, et al., Capillary Condensation of Binary and Ternary Mixtures of n-Pentane-Isopentane-CO2 in Nanopores: An Experimental Study on the Effects of Composition and Equilibrium, Langmuir 2018, 34, pp. 1967-1980.
(Continued)

*Primary Examiner* — Francis C Gray
(74) *Attorney, Agent, or Firm* — Patterson + Sheridan, LLP

(57) ABSTRACT

Embodiments of the present disclosure generally relate to apparatus, systems, and methods for characterizing fluid-solid systems. In an embodiment, a method includes placing a porous rock sample in a core holder, contacting the porous rock sample with a fluid to create a fluid-solid system inside the core holder, automatically adjusting a temperature and/or pressure of the fluid-solid system to a preselected value via a processor and at least one automated valve, monitoring the fluid-solid system for equilibrium, recording a value for temperature, pressure, and/or mass of the fluid-solid system, performing an action based on the recorded data, and repeating the adjusting, monitoring, recording, and performing operations to produce a thermodynamic data characteristic of the fluid-solid system. In one example, the performing operation includes analyzing a pressure signal for stationarity by performing an Augmented Dickey-Fuller (ADF) test and/or a Kwiatkowski-Phillips-Schmidt-Shin (KPSS) test.

20 Claims, 12 Drawing Sheets

(51) Int. Cl.
    *G01N 33/24*    (2006.01)
    *G01N 30/06*    (2006.01)

(56) References Cited

U.S. PATENT DOCUMENTS

| | | | |
|---|---|---|---|
| 2013/0125630 A1* | 5/2013 | Collins | G01N 1/00 73/64.56 |
| 2014/0309782 A1* | 10/2014 | Sharpe | G01N 15/1404 700/266 |
| 2018/0148988 A1 | 5/2018 | Dusterhoft et al. | |
| 2018/0321120 A1* | 11/2018 | Piri | G01N 5/02 |
| 2019/0303783 A1 | 10/2019 | Utsumi et al. | |
| 2022/0091572 A1* | 3/2022 | Biernat | G06F 9/5083 |

OTHER PUBLICATIONS

International Search Report and Written Opinion for International Application No. PCT/US2022/028466 dated Aug. 17, 2022.

\* cited by examiner

AUTOMATED APPARATUS FOR CHARACTERIZATION OF FLUID-SOLID SYSTEMS

CROSS-REFERENCES TO RELATED APPLICATIONS

This application claims priority to U.S. Provisional Patent Application No. 63/186,366, filed May 10, 2021, which is incorporated herein by reference in its entirety.

BACKGROUND

Field

Embodiments of the present disclosure generally relate to apparatus, systems, and methods for studying interactions between fluids and solids and for characterizing fluid-solid systems.

Description of the Related Art

The interactions between fluids and solids may be studied via recording mass and/or composition of a certain fluid as a function of time (time series data). For adsorption/desorption and capillary condensation phenomena, the term gravimetric is used where the mass of the fluid indicates its phase behavior. U.S. Pat. No. 10,302,540 discloses an apparatus for studying a fluid-solid system. An embodiment of the apparatus of U.S. Pat. No. 10,302,540 is shown in FIG. 1. The apparatus shown in FIG. 1 is generally operated manually, as each point of pressure change must be decided and manually executed by human interaction. This manual nature of the apparatus causes it to be idle for extended periods of times and hence its full potential is not fully utilized.

There is a need for new and improved apparatus, systems, and methods for studying interactions between fluids and solids and for characterizing fluid-solid systems.

SUMMARY

Embodiments of the present disclosure generally relate to apparatus, systems, and methods for studying interactions between fluids and solids and for characterizing fluid-solid systems.

In an embodiment, an apparatus for characterizing a fluid-solid system is provided. The apparatus includes a core holder, and a pressure sensor coupled to the core holder, the pressure sensor configured to sense a pressure within the core holder and produce a pressure signal. The apparatus further includes a mass comparator operationally connected to an interior of the core holder. The apparatus further includes a pressure and flow control system comprising: a pressure source in selective fluid communication with the core holder; an automated pressure valve configured to control pressure within the core holder; and a processor configured to: control the automated pressure valve based at least in part on the pressure signal; and log data from the pressure sensor and the mass comparator.

In another embodiment, a method of characterizing a fluid-solid system is provided. (a) contacting a porous rock sample, disposed within a core holder, with a fluid to form a fluid-solid system inside the core holder; and (b) automatically adjusting a temperature of the fluid-solid system, a pressure of the fluid-solid system, or both, to a preselected value via a processor and at least one automated valve. The method further includes (c) monitoring the fluid-solid system for equilibrium. The method further includes (d) recording a value for temperature, a value for pressure, a value for mass, or a combination thereof, of the fluid-solid system, to provide recorded data. The method further includes (e) performing an action based on the recorded data. The method further includes (f) repeating operations (b) through (e) to produce a thermodynamic data characteristic of the fluid-solid system.

In another embodiment, a method of characterizing a fluid-solid system includes (a) introducing a fluid with a porous rock sample disposed within a core holder to form a fluid-solid system inside the core holder. The method further includes (b) automatically adjusting a pressure of the fluid-solid system to a preselected value via a processor and at least one automated valve, wherein the automatically adjusting comprises: performing a series of short valve openings in order to generate a series of data; and analyzing the series of data in order to calculate the calculated period of time. The method further includes (c) monitoring the fluid-solid system for equilibrium by a pressure sensor; and (d) recording a value for pressure, a value for mass, or a combination thereof, of the fluid-solid system, to provide recorded data; analyzing a pressure signal for stationarity by performing an Augmented Dickey-Fuller (ADF) test, a Kwiatkowski-Phillips-Schmidt-Shin (KPSS) test, or both, the pressure signal corresponding to the pressure within the core holder. The method further includes (e) performing an action based on the recorded data. The method further includes (f) repeating one or more of operations (b) through (e) to produce a thermodynamic data characteristic of the fluid-solid system.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

Figure 1:
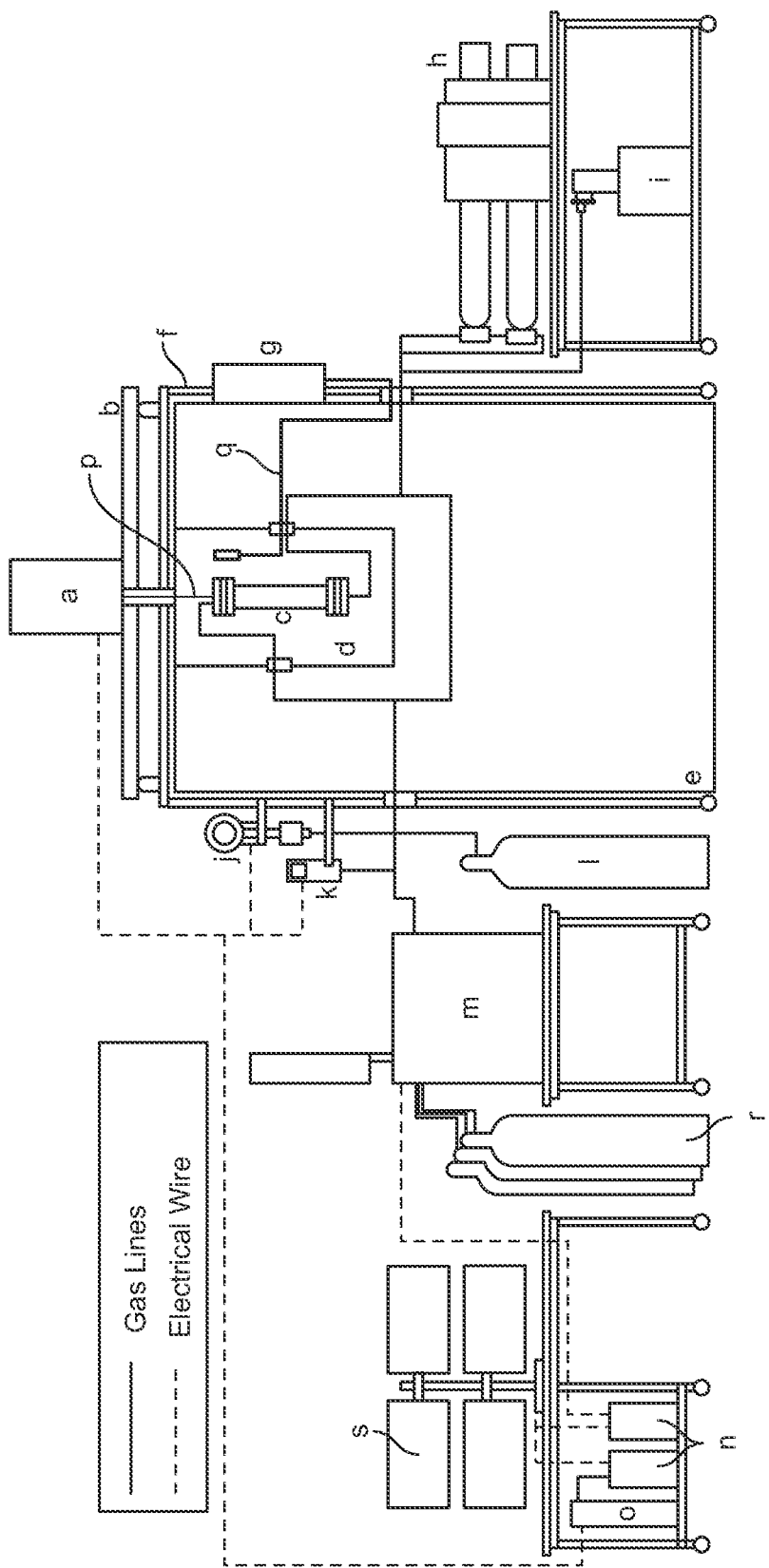
FIG. 1 shows a schematic diagram of one embodiment of an apparatus for characterizing a fluid-solid system according to at least one embodiment of the present disclosure.

In the following description, numerous specific details of the apparatus, systems, and methods of the present disclosure are set forth in order to provide a thorough explanation of the precise nature of the disclosure. It will be apparent, however, to those of skill in the art that the disclosure can be practiced without these specific details.

DETAILED DESCRIPTION

Embodiments of the present disclosure generally relate to apparatus, systems, and methods for studying interactions between fluids and solids and for characterizing fluid-solid systems. The apparatus, systems, and methods for characterizing a fluid-solid system can be used to study phase interactions within a sample. The sample may be static or dynamic and be comprised of fluid (for example, gas and/or liquid) and solid aggregate states. Phase interactions may include adsorption, desorption, and capillary condensation, and may be analyzed gravimetrically via recordings of mass and/or composition of the fluid as a function of time. Effects of environmental parameters such as temperature and pressure on the aforementioned interactions may also be studied and characterized via use of apparatus, systems, and methods described herein.

In general, the terms and phrases used herein have their art-recognized meaning, which can be found by reference to standard texts, journal references and contexts known to those skilled in the art. The following definitions are provided to clarify their specific use in the context of the present disclosure.

As used herein, the term "environmental chamber" refers to an enclosure in which environmental parameters including temperature, pressure and humidity can be controlled. An environmental chamber may be used to test specific conditions on samples or experiments or to store sensitive materials. As such, environmental chambers may differ greatly in size and equipment. In one embodiment, the "environmental chamber" is equipped with sample holders outfitted with pressure transducers and differential mass balances (or mass comparators) feeding measurement data into a data acquisition box. In some embodiments, the environmental chamber functions as a thermostat, capable of temperature control of ±0.1 K.

As used herein, the term "core holder" refers to an apparatus for holding a porous sample. The core holder may be used for fluid permeability experiments. Conditions within the core holder may be measured and applied to the sample. In some embodiments, pressure within the core holder may be measured using a pressure sensor. In at least one embodiment, changes in mass within the core holder may be measured via a mass comparator.

As used herein, the term "selective fluid communication" refers to the arrangement of two or more elements of an apparatus such that a fluid can be transported to, past, through or from one object to another selectively. For example, two elements are in selective fluid communication with one another if a fluid flow path including one or more valves is provided between the two elements. Accordingly, the flow path may be selectively opened or closed via, for example, operation of the one or more valves.

As used herein, the term "stationarity" refers to the degree to which a time series is stationary. A time series may be stationary if the mean and variance of a distribution of the time series remain unchanged over a period of time. A time series is not stationary if there is a trend in the mean. Stationarity can be evaluated by performing one or more hypothesis tests, which include but are not limited to an Augmented Dickey-Fuller (ADF) test, a Zivot-Andrews Test, and a Kwiatkowski-Philips-Schmidt-Shin (KPSS) test. As used herein, the stationarity of the pressure signal indicating the pressure within the core holder is analyzed using an automated algorithm. In said algorithm, an augmented ADF test is testing the null hypothesis of a unit root being present in the pressure data while a KPSS test examines if a time series remains stable around a mean, or if a unit root is present. The level of stationarity negatively correlates to the value assigned to the ADF test. The more negative the number, the stronger the rejection of the hypothesis of the existence of a unit root and the more stationary the measurement data.

As used herein, the term "atmospheric purge mechanism" refers to a mechanism that replaces atmospheric air contained in a closed system with a purge gas. In some embodiments, the purge gas may comprise a non-reactive gas. Thus, in some embodiments, an atmospheric purge mechanism may create an oxygen deficient and non-combustible environment. Non-reactive gases can be inert gases and therefore can be used to prevent unwanted chemical reactions from happening. Any suitable non-reactive gas can be used. Illustrative, but non-limiting, examples of non-reactive gases used for the purge gas include nitrogen, argon helium, neon, krypton, xenon, argon, carbon dioxide, and combinations thereof. An atmospheric purge mechanism may include flushing the respective system with a non-reactive purge gas. As used herein, the non-reactive gas is introduced to the environmental chamber via an automated purge valve.

As used herein, the term "porous rock sample" refers to a specimen representing rock material containing minute cavities. The minute cavities of a porous rock sample may be contain liquids and/or gases. The size, structure, and distribution of these cavities determines the porosity of a given sample. In some embodiments, the porous rock sample may be a nanoporous material. Nanoporous materials may include a framework or matrix with a structure of pores, each being about 100 nm or smaller and can be subdivided into three categories: microporous (pore sizes between about 0.2 nm and about 2 nm), mesoporous (pore sizes between about 2 nm and about 50 nm), and macroporous (pore sizes between about 50 nm and about 1000 nm). In some embodiments, porous rock samples may include surface-modified silica MCM-41 samples. The minute cavities of the surface-modified silica MCM-41 samples may contain n-butane and iso-butane functioning as model fluid.

As used herein, the term "fluid-solid system" refers to a system that includes at least one fluid phase and at least one solid phase. Phase interactions of a fluid-sold system may be dynamic or static. Phase interactions of the fluid-solid system may be characterized by structural mechanics, fluid dynamics, and/or thermodynamics. In some examples, a fluid-solid system includes a porous rock sample and a fluid contained within a core holder.

As used herein, the term "coupled", including its various forms such as "operably coupling", "coupling" or "couplable", refers to the joining of two components or parts directly or indirectly, and comprises direct or indirect, structural coupling or electrical coupling, connection or attachment, or adaptation or capability for such a direct or indirect structural, electrical or operational coupling, connection or attachment, including integrally formed components and components which are coupled via or through another component. Indirect coupling may involve coupling through an intermediary component or part. Coupled can also include components that are remote coupled and coupled by transmitters and receivers.

As used herein, the term "capillary condensation" refers to the process by which a fluid in vapor phase adsorbs into a porous medium, builds multiple layers of the adsorbed vapor phase, and at a certain temperature and pressure nucleates into a condensed phase that fills the pores of the porous medium. The term "capillary condensation" and "nanocondensation" are used interchangeably unless the context indicates otherwise.

FIG. 1 shows an apparatus disclosed in U.S. Pat. No. 10,302,540, which is incorporated by reference in its entirety to the extent not inconsistent with the disclosure in this application. The apparatus shown in FIG. 1 is operated manually, as each point of pressure change must be decided and manually executed by human interaction. This manual nature of the apparatus causes it to be idle for extended periods of times and hence its full potential is not fully utilized. In addition, the amount of data (and final output resolution) generated with manual operation is much lower than what could be accomplished with the automated system. Table 1 shows a list of certain parts of the apparatus shown in FIG. 1.

TABLE 1

| Ref. | Part |
| --- | --- |
| (a) | Balance or mass comparator |
| (b) | Anti-vibration table |
| (c) | Core holder |
| (d) | Draft shield |
| (e) | Environmental chamber |
| (f) | Frame |
| (g) | Thermocouple power supply and data logger |
| (h) | Dual cylinder pump |
| (i) | Turbomolecular pump |
| (j) | Pressure transducer |
| (k) | Vacuum gauge |
| (l) | Gas cylinders |
| (m) | Gas chromatograph |

TABLE 1-continued

| Ref. | Part |
| --- | --- |
| (n) | Computers |
| (o) | Data acquisition box |
| (p) | Insulated wire |
| (q) | Thermocouple wire |
| (r) | Chromatographic gases |
| (s) | Monitors |

Apparatus disclosed herein, in contrast, can include various additional elements that can enable automation among other advantages. For example, and in addition to one or more of the parts (a)-(s), apparatus described herein can include one or more of an electric valve, a remote-control unit, and an advanced computer algorithm. For clarity, and in the apparatus shown in FIGS. 2-6, one or more of the parts (a)-(s) can be utilized even though one or more of such parts are not shown. Apparatus described herein can be a gravimetric apparatus.

Figure 2:
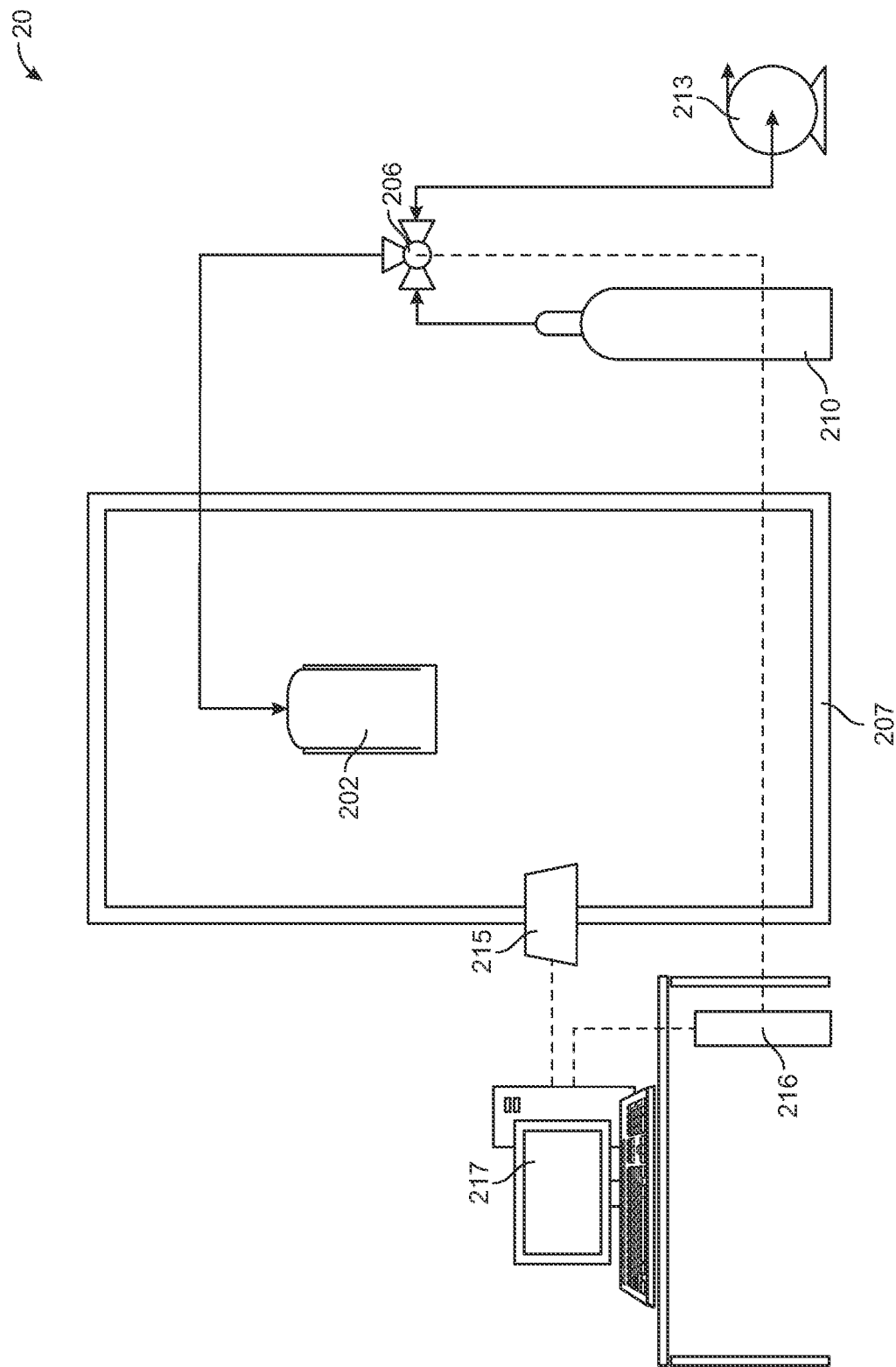
FIG. 2 shows an example of an example automated apparatus for characterizing a fluid-solid system according to at least one embodiment of the present disclosure.

Beyond automation, apparatus of the present disclosure can maintain a variety of fluids at specific temperatures (e.g., temperatures in a range from about −100° C. to about 232° C.) and pressures (e.g., pressures in a range from vacuum to about 10,000 psi). In addition, apparatus described herein can have the ability to simulate overburden pressure. Consequently, apparatus of the present disclosure may be used to study interactions between fluids and solids, including adsorption, desorption, and nanocondensation (also known as "capillary condensation"). In particular, apparatus described herein may be used to reconstruct reservoir conditions during capillary condensation measurements. Further, apparatus of the present disclosure may be used to achieve the temperatures and pressures necessary to study single-component fluids in a variety of adsorbent pore types. FIG. 2 shows an example setup for an apparatus described herein.

FIG. 2 shows an example of an apparatus 20 for characterizing a fluid-solid system according to at least one embodiment of the present disclosure. As stated above, one or more parts of the apparatus shown in FIG. 1 can be utilized with apparatus of the present disclosure. A brief description of such parts shown in FIG. 1 is provided below.

Balances are used to measure an amount of fluid adsorbed or desorbed. To enable high resolution and a large maximum load to study capillary condensation at reservoir conditions, a mass comparator (a) can be used instead of a traditional balance according to some embodiments. Here, traditional balances have insufficient capacity and resolution. Unlike traditional balances, mass comparators weigh by difference, allowing for high resolution with large maximum loads. For example, a Mettler Toledo XPE505C mass comparator has a resolution of 0.01 milligrams even at its maximum load of 520 grams. Other suitable mass comparators and balances are contemplated. The mass comparator (a) may be placed on top of an anti-vibration table (b).

Apparatus of the present disclosure can accommodate an entire core and core holder (c) with a mass of up to the maximum load of the mass comparator (a) used in the apparatus. For example, when the apparatus uses a Mettler Toledo XPE505C mass comparator, the apparatus can accommodate an entire core and core holder with a mass of up to about 520 g. Other suitable mass comparators can accommodate other suitable masses. Fluid lines, which may be flexible, can be used to introduce fluid to the core holder (c) and can allow for the forced flow of fluids through the core holder (c). Accordingly, and in some embodiments, apparatus described herein can enable investigations of both single-component and multicomponent fluids in both static and flow-through measurements.

Various types of core holder (c) can be used with apparatus described herein. Suitable core holders include those utilized in petroleum engineering research, including those that can sustain high pressure, high temperature reservoir condition experiments. Suitable core holders may also be modified for the application of overburden stress.

Illustrative, but non-limiting, examples of core holders include those used for studies of simple fluids in ideal adsorbents as described in, at least, FIGS. 2-8 of U.S. Pat. No. 10,302,540. A first type of core holder comprises a body, endcaps, a hanging plate, filters, compression fittings, and a modified compression spring. The core holder body may be made out of titanium, stainless steel, carbon fiber, or other suitable materials. The core holder body can have: an internal diameter in the range of about 0.1 inch (in.) to about 2 in., such as from about 0.5 in. to about 1.5 in., such as about 0.75 in.; an external diameter in the range of about 0.1 in. to about 2 in., such as from about 0.5 in. to about 1.5 in., such as about 1.0 in.; and a length in the range of about 4 in. to about 10 in., such as from about 4 in. to about 7 in., such as about 4 in. Other dimensions are contemplated.

Endcaps of the core holder may be made out of titanium, stainless steel, or other suitable materials. Dimensions of various elements of endcaps—for example, a curvature of the internal diameter, an external diameter, a diameter of the port for a compression fitting, an internal diameter, and a length of the thread—can include those typically used. For example, the curvature of the internal diameter of the endcap can be in the range of about 0 in. to about 0.05 in, such as in the range of about 0 in. to about 0.03 in., such as about 0.03 in. The external diameter of the endcap may be in the range of about 0.1 in to about 0.2 in., such as in the range of about 0.5 in. to about 1.5 in., such as about of 0.746 in. The diameter of the port for the compression fitting of the endcap may be in the range of about 0.015 in. to about 0.5 in., such as in the range of about 0.05 in. to about 0.25 in., such as about 0.242 in. The internal diameter of the endcap may be in the range of about 0.1 in. to about 2 in., such as in the range of about 0.5 in.1.5 in., such as about 0.600 in. The length of the thread of the endcap may be in the range of about 0.5 in. to about 3 in., such as in the range of about 0.5 in. to about 1.5 in., such as about 0.625 in. or about 2 in. Other dimensions are contemplated. An illustrative, but non-limiting, example of the first type of core holder that can be used with embodiments described herein is shown in FIG. 2 of U.S. Pat. No. 10,302,540.

Figure 6:
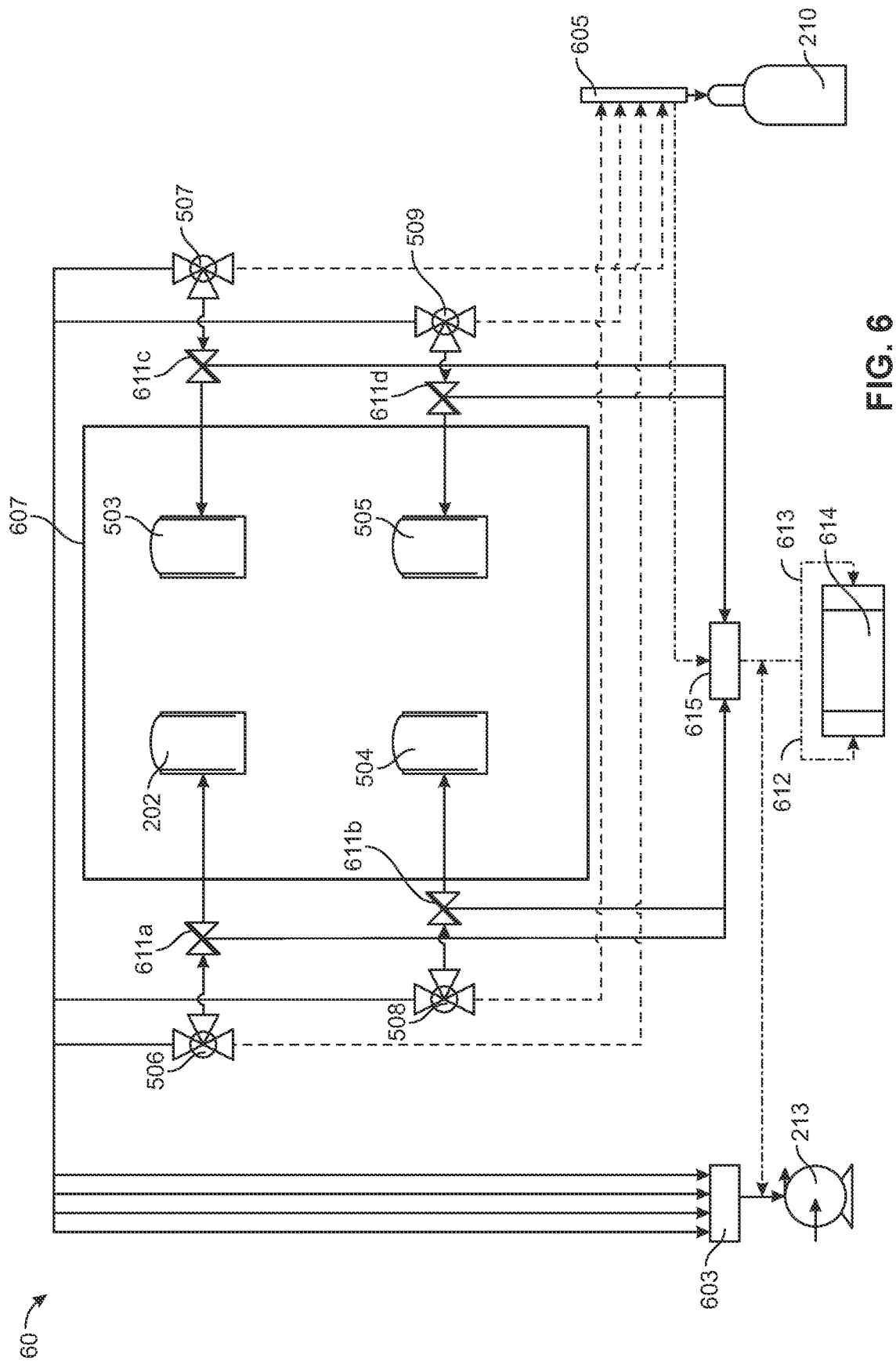
FIG. 6 shows a top schematic view of the example apparatus shown in FIG. 5, including the independence of each core holder and the integration with the gas chromatograph, according to at least one embodiment of the present disclosure.

A second type of core holder includes a body, endcaps, a hanging plate, filters, compression fittings, and a modified compression spring. The second type of core holder further includes a flexible cylinder encapsulated inside the body of the core holder. The second type of core holder can tolerate high pressures (up to about 10,000 psi), high temperatures (up to 232° C.), and the application of overburden stress and may be used for advanced experiments, including experiments on reservoir fluids and reservoir rocks (for example, 1 inch core plugs, 1.5 inch core plugs, and crushed rock). For example, the second type of core holder may be used in advanced studies of capillary condensation in the presence of overburden pressure. Overburden fluid (for example, mineral oil) may be pumped into the void between the flexible cylinder and the body of the core holder to supply a confining pressure, simulating overburden. As another example, in flow-through experiments, one cylinder of a dual cylinder pump (such as a Quizix pump) may control the pressure of fluids flowing into the second type of core holder, while the other cylinder of the dual cylinder pump may be used to provide back pressure. An illustrative, but non-limiting, example of the second type of core holder that can be used with embodiments described herein is shown in FIG. 6 of U.S. Pat. No. 10,302,540.

A third type of core holder may be used to apply overburden pressure by mechanical means. The third type of core holder includes a body, endcaps, a hanging plate, filters, compression fittings, and a modified compression spring. The third type includes either: endcaps (having a length of, for example, about 0.5 in. to about 1.5 in.) that are lengthened by attaching a spacer having a length of, for example, about 0.5 in. to about 1.5 in.) to the endcap, such that the total length of the endcap+spacer combination is, for example, about 1 in. to about 3 in.; or long endcaps (having a length of, for example, about 1 in. to about 3 in.). By tightening the encap+spacer combination or by tightening the long endcap, mechanical pressure can be applied to the core. An illustrative, but non-limiting, example of the second type of core holder that can be used with embodiments described herein is shown in FIGS. 7A and 7B of U.S. Pat. No. 10,302,540.

A fourth type of core holder may be used to apply overburden pressure by mechanical means. The fourth type of core holder includes a body, endcaps, a hanging plate, filters, compression fittings, and a modified compression spring. The fourth type of core holder further includes a sleeve on the outside of the core body with a hand crank on the surface of the sleeve. By turning the hand crank one way, the sleeve—and therefore the core body—constricts, causing pressure that squeezes the core. An illustrative, but non-limiting, example of the second type of core holder that can be used with embodiments described herein is shown in FIGS. 7A and 7B of U.S. Pat. No. 10,302,540.

The mass comparator (a) is positioned on top of an environmental chamber (e) while hanging an adsorbent inside the environmental chamber (e) from a hook or insulated wire (p) on the bottom of the mass comparator (a). Such a configuration can serve to protect a mass comparator's sensitive electronics in experiments carried out at extreme conditions (e.g., reservoir temperatures and reservoir pressures). Other protective measures include containing experimental pressures within high pressure, high temperature tubing and the core holder, which houses the adsorbent.

An environmental chamber (e) is used to ensure, for example, precise temperature control of the apparatus. The environmental chamber (e) may be customized to include an extended lower operating temperature of −100° C., an extended upper operating temperature of 232° C., the capacity to interface with four or more resistance temperature detectors (RTDs) and two or more thermocouples, and ports on both the sides and on top of the chamber. Including ports on both the sides and on top of the environmental chamber (e) may be useful to pass lines and wires into and out of the environmental chamber (e), including the wire suspending the core holder (c) from the mass comparator (a). For example, thermocouple and/or RTD wires (q) may be inside the environmental chamber (e) and the thermocouple and/or RTD box (e.g., the thermocouple power supply and data logger (g)) may be placed outside the environmental chamber (e). The ports may also be useful to anchor a homemade draft shield (d), which may be fastened around the core holder to prevent air currents in the environmental chamber (e) from impairing the resolution of the mass comparator (a). An illustrative, but non-limiting, example of an environmental chamber (e) is Thermotron XSE-600-3-3-MS. Other environmental chambers or suitable apparatus for controlling temperature are contemplated.

In addition, the environmental chamber (e) may be purged with a non-reactive gas (e.g., gaseous nitrogen). Purging the environmental chamber with a non-reactive gas can increase the safety of high-pressure, high-temperature reservoir condition experiments. Also, purging the environmental chamber with a non-reactive gas can help mitigate or prevent ice formation during low temperature experiments. The non-reactive gas may be stored in one or more of the gas cylinders (l) outside of the environmental chamber (e) and filtered through a gas dryer (not shown) prior to entering the environmental chamber (e). A frame (f), or support structure, can be placed over the environmental chamber (e).

A pump (h) is to pressurize fluids under study. An illustrative, but non-limiting, example of a pump (h) is a dual cylinder Q6000 Quizix pump. Other pumps or suitable apparatus for pressurizing fluids are contemplated. If the pump (h) has a high maximum operating temperature, it can be housed outside of the environmental chamber (e). For example, a dual cylinder Q6000 Quizix pump has a maximum operating temperature of 160° C. and can be housed outside of the environmental chamber (e). Other pumps may have lower or higher maximum operating temperatures and may be housed either outside or inside of the environmental chamber (e). In some embodiments, both cylinders of the pump (h) can be used to pressurize fluids. In experiments utilizing the injection of pre-heated fluids, heating tape may be used to heat the cylinders of the pump (h). The use of heating tape can serve as an alternative to housing the cylinders of the pump (h) inside of the environmental chamber (e).

A turbo-molecular pump (i) may be used in the apparatus to vacuum out the system and de-gas the adsorbent. The turbo-molecular pump (i) can be a hydrocarbon-free turbo-molecular pump. A hydrocarbon-free turbo-molecular pump has magnetic bearings instead of oil-lubricated bearings. Consequently, lubricant fumes do not adsorb to tubing during vacuuming. Hydrocarbon-free turbo-molecular pumps can achieve vacuum levels of at least $10^{-6}$ mbar.

A data acquisition box (o) is positioned outside of the environmental chamber. The data acquisition box (o) is utilized to acquire data from various parts of the apparatus such as the mass comparator (a) and the thermocouple power supply and data logger (g). The data acquisition box (o) is coupled to the mass comparator (a) and the thermocouple power supply and data logger (g) via electrical wires (indicated as dashed lines). Mass readings are taken from the mass comparator (a). The data acquisition box (o) is also coupled to a pressure transducer (j) and a vacuum gauge (k), which are positioned outside of the chamber, and are used to take pressure readings. Any suitable pressure transducer and vacuum gauge can be used.

A gas chromatograph (m) can be used in the apparatus to monitor the concentrations of fluids adsorbed and desorbed for the advanced study of multi-component fluids. Chromatographic gasses (r) are coupled to the gas chromatograph (m). A computer (n) and monitors (s) are utilized to, e.g., control the gas chromatograph (m) and view experimental results. An illustrative, but non-limiting, example of a gas chromatograph (m) that can be used is an Agilent 7890B. Other suitable gas chromatographs are contemplated.

The gas chromatograph (m) may be customized to analyze all fluids encountered in capillary condensation experiments. For example, the gas chromatograph (m) may be customized to be capable of Detailed Hydrocarbon Analysis to study hydrocarbon fluids. Further, the gas chromatograph (m) may be customized to be capable of Simulated Distillation for crude oil. In addition, the gas chromatograph (m) may be customized to be capable of analyzing fixed gases (e.g., nitrogen and carbon dioxide). The plumbing of the gas chromatograph (m) may be made out of suitable materials such as Hastelloy, and may be fitted with high-pressure (e.g., 3000 psi) and/or heated gas inlet valve to ensure the proper analysis of reservoir fluids.

The gas chromatograph (m) may also be used to measure the composition of a bulk fluid and/or the composition of a confined fluid. To measure the composition of confined fluid, for example, a liquid nitrogen trap can be used to draw the confined fluid out of an adsorbent in the core holder (c). The confined fluid is collected from the liquid nitrogen trap and then transferred to the gas chromatograph (m) for analysis.

Various parts or components of the apparatus shown in FIG. 1 can be used with other apparatus described herein, such as those apparatus illustrated in FIGS. 2-6. Similarly, various parts or components of the apparatus in each of FIGS. 1-6 can be suitably used with one or more other apparatus described herein.

Returning to FIG. 2, the apparatus 20 includes a core holder 202 disposed within the environmental chamber 207. The environmental chamber 207 and the core holder 202 may be the same as, or different from, the environmental chamber and core holder described in relation to FIG. 1. An environmental chamber control unit 215 can be utilized to control operation of the environmental chamber 207. The environmental chamber 207 can include a heating element, a cooling element, and a temperature sensor. The environmental chamber 207 comes equipped with the heating element, a cooling element, and a temperature sensor. The environmental chamber 207 can further include an atmospheric purge mechanism configured to purge the interior of the environmental chamber 207 of, e.g., oxygen. The environmental chamber 207 comes equipped with the automated purge mechanism. A source of non-reactive gas can be in selective fluid communication with the interior of the environmental chamber. An automated purge valve can be positioned between the source of non-reactive gas and the environmental chamber 207, and can be configured to control a flow of the non-reactive gas into the environmental chamber 207. A three-way valve 206 (which may be, for example, a remotely actuated three-way valve) is coupled to the core holder 202, a gas tank 210 (or gas cylinder), and a vacuum pump 213 (or vacuum source) by lines, piping, or tubing. The three-way valve 206 is configured to control the flow of, e.g., gas and vacuum through various portions of the apparatus 20. The three-way valve 206 can free the apparatus 20 of manual actuation, enabling remote and automatic injection and/or suction of fluids. The three-way valve 206 can also enable selective fluid communication of vacuum, gas, and/or pressure with the core holder 202. In FIG. 2, electrical wire or connection is indicated by the dashed lines while gas and vacuum lines are indicated by the solid lines. Instead of electrical wire and connection, transmitters and receivers can be used to send signals to various components of the apparatus 20.

The apparatus 20 may further include a pressure sensor or pressure transducer (not shown) configured to sense the pressure inside or within the core holder 202 and produce a pressure signal. The pressure sensor or pressure transducer can be similar to pressure transducer (j) and is operationally connected to the interior of the core holder. The apparatus 20 may further include a mass comparator (not shown) configured to sense mass changes within the core holder 202. The mass comparator, which can be similar to the mass comparator (a), is operationally connected to the interior of the core holder 202. The apparatus 20 may further include a pressure and flow control system that generally includes a pressure source in selective fluid communication with the core holder, an automated pressure valve (e.g., three-way valve 206) configured to control pressure within the core holder, and a processor. The processor, further described below, execute instructions of algorithms described herein. The apparatus 20 may further include an automated vacuum valve (e.g., three-way valve 206) configured to control pressure within the core holder. The automated vacuum valve (e.g., three-way valve 206) can be coupled to the vacuum pump 213 and to the core holder 202.

As described, the three-way valve 206 has multiple functions, such as e.g., controlling the pressure within the core holder. The three-way valve 206 is in selective communication with the pressure source. The three-way valve 206 is in selective communication with the vacuum source. The three-way valve 206 is also referred to as an automated valve.

In the illustrated embodiment, the three-way valve 206 is a constant volume, remotely actuated three-way valve, however, other valves are contemplated. The three-way valve 206 may be a rapid open/close valve wherein opening or closing is completed in, e.g., approximately 0.1 second, though other values are contemplated. In some embodiments, the three-way valve 206 is actuated using compressed air supplied at, for example, 70-100 psi, via a solenoid pilot valve (12V or 24V) installed in the data acquisition and remote control unit 216.

The apparatus 20 further includes a data acquisition and remote control unit 216 operably coupled to the three-way valve 206 and the computer 217. The data acquisition and remote control unit 216 can also be operably coupled to mass comparator(s), pressure sensor(s), pressure transducer(s), thermocouple(s), vacuum gauge(s), among other components.

The computer 217 can be utilized to send information, e.g., commands, to the data acquisition and remote control unit 216 The data acquisition and remote control unit 216 can be utilized to control various components of the apparatus and to view experimental results. The data acquisition and remote control unit 216 can be any suitable unit. Data acquisition and remote control units can include sensors to convert physical parameters to electrical signals; signal conditioning circuitry, to convert sensor signals into a form that can be converted to digital values; analog-to-digital converters, to convert conditioned sensor signals to digital values. Computer software associated with the data acquisition and remote control unit 216 processes raw data from various components of the apparatus, such as a mass comparator, thermocouple(s), pressure transducer(s), vacuum gauge(s), among other components. A computer algorithm is utilized to, e.g., process the data from the data acquisition and remote control unit 216 and make decisions on remotely opening/closing valves, among other operations. Illustrative, but non-limiting embodiments of the computer algorithm are described below and a simplified activity diagram is presented in FIG. 7.

The data acquisition and remote control unit 216 is operable to control one or more operations of the apparatus, systems, and/or methods described herein via the data acquisition and remote control unit 216. The data acquisition and remote control unit 216 includes one or more processors, memory, and support circuits. The processor may be one of any form of general purpose microprocessor, or a general purpose central processing unit (CPU), each of which can be used in an industrial setting, such as a programmable logic controller (PLC), supervisory control and data acquisition (SCADA) systems, or other suitable industrial controller.

The one or more processors of the data acquisition and remote control unit 216 can execute instructions of algorithms described herein. The processor can be configured to perform one or more of the following operations: (a) control an automated pressure valve (e.g., the three-way valve 206) based at least in part on pressure signals from a pressure sensor; (b) to step the pressure within the core holder 202 through a series of predetermined pressure set points; (c) to control the pressure within the core holder 202 to a predetermined pressure set point; (d) to analyze pressure signals for stationarity; (e) to open and/or close the automated pressure valve (e.g., the three-way valve 206) for a calculated period of time to control the pressure within the core holder 202 to a predetermined pressure set point; (f) to control an automated vacuum valve (e.g., the three-way valve 206); (g) to control the temperature within the environmental chamber 207; (h) to control the atmosphere within the environmental chamber 207 via an automated purge valve; (i) to automatically direct the contents of the core holder 202 into the gas chromatograph (discussed below, e.g., gas chromatograph 614); (j) to automatically log data from the pressure sensor, the mass comparator, and other components; (k) to control the atmosphere within the environmental chamber 207 via the automated purge valve coupled to the environmental chamber 207.

Although the one or more processors are discussed with reference to FIG. 2, the one or more processors can be used with other apparatus described herein, such as the apparatus of FIGS. 1-6.

The one or more processors can additionally be configured to analyze the pressure signal for stationarity by an Augmented Dickey-Fuller (ADF) test and/or a Kwiatkowski-Phillips-Schmidt-Shin (KPSS) test as further described below. The one or more processors can be configured to calculate the calculated period of time by performing a series of short valve openings in order to generate a series of data; and analyzing the series of data in order to calculate the calculated period of time.

The memory is non-transitory and may be one or more of readily available memory such as random access memory (RAM), read only memory (ROM), or any other form of digital storage, local or remote. The memory contains instructions, that when executed by the processor, facilitates the operation of apparatus described herein and methods described herein. The instructions in the memory are in the form of a program product such as a program that implements the method of the present disclosure. The program code of the program product may conform to any one of a number of different programming languages. Illustrative computer-readable storage media include, but are not limited to: (i) non-writable storage media (e.g., read-only memory devices within a computer such as CD-ROM disks readable by a CD-ROM drive, flash memory, ROM chips, or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods described herein, are examples of the present disclosure. In one example, the disclosure may be implemented as the program product stored on a computer-readable storage media (e.g., memory) for use with the data acquisition and remote control unit 216 and the computer 217. The program(s) of the program product define functions of the disclosure, described herein.

In the illustrated embodiment of FIG. 2, a fluid-solid system may be tested across a series of pressure, temperature, and or density ranges or points in order to characterize a particular fluid-solid system. For example, a porous rock sample may be placed in the core holder 202 and a gaseous fluid may be introduced to the porous sample in core holder via gas tank 210, thereby creating a fluid-solid system. At least a portion of the gaseous fluid may condense in and/or on the porous rock sample, as detected by the mass comparator.

The data acquisition and remote control unit 216 may be configured to automatically adjust temperature and/or pressure of the fluid-solid system to a preselected value. For example, the pressure of the fluid-solid system can be controlled by actuating the three-way valve 206 to increase pressure via the gas tank 210 or decrease pressure via the vacuum pump 213. The data acquisition and remote control unit 216 may be configured to automatically monitor the fluid-solid system for equilibrium via, for example, the pressure sensor. The data acquisition and remote control unit 216 may be configured to automatically record a value for temperature, pressure and/or mass of the fluid-solid system. The data acquisition and remote control unit 216 may then direct the apparatus to adjust the pressure and/or temperature inside the core holder 202.

Figure 3:
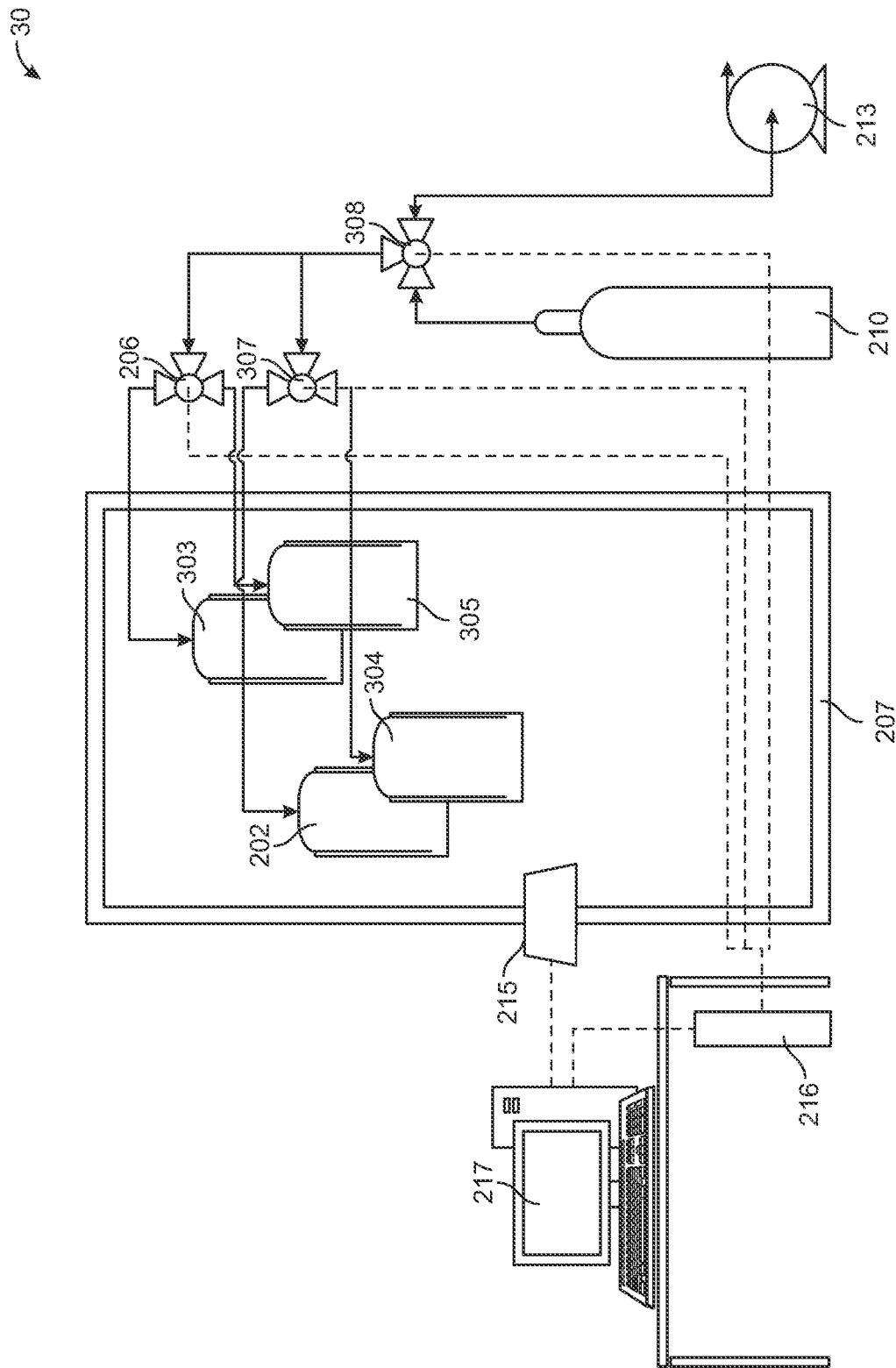
FIG. 3 shows an elevation schematic of an example automated apparatus for characterizing a fluid-solid system according to at least one embodiment of the present disclosure.
Figure 4:
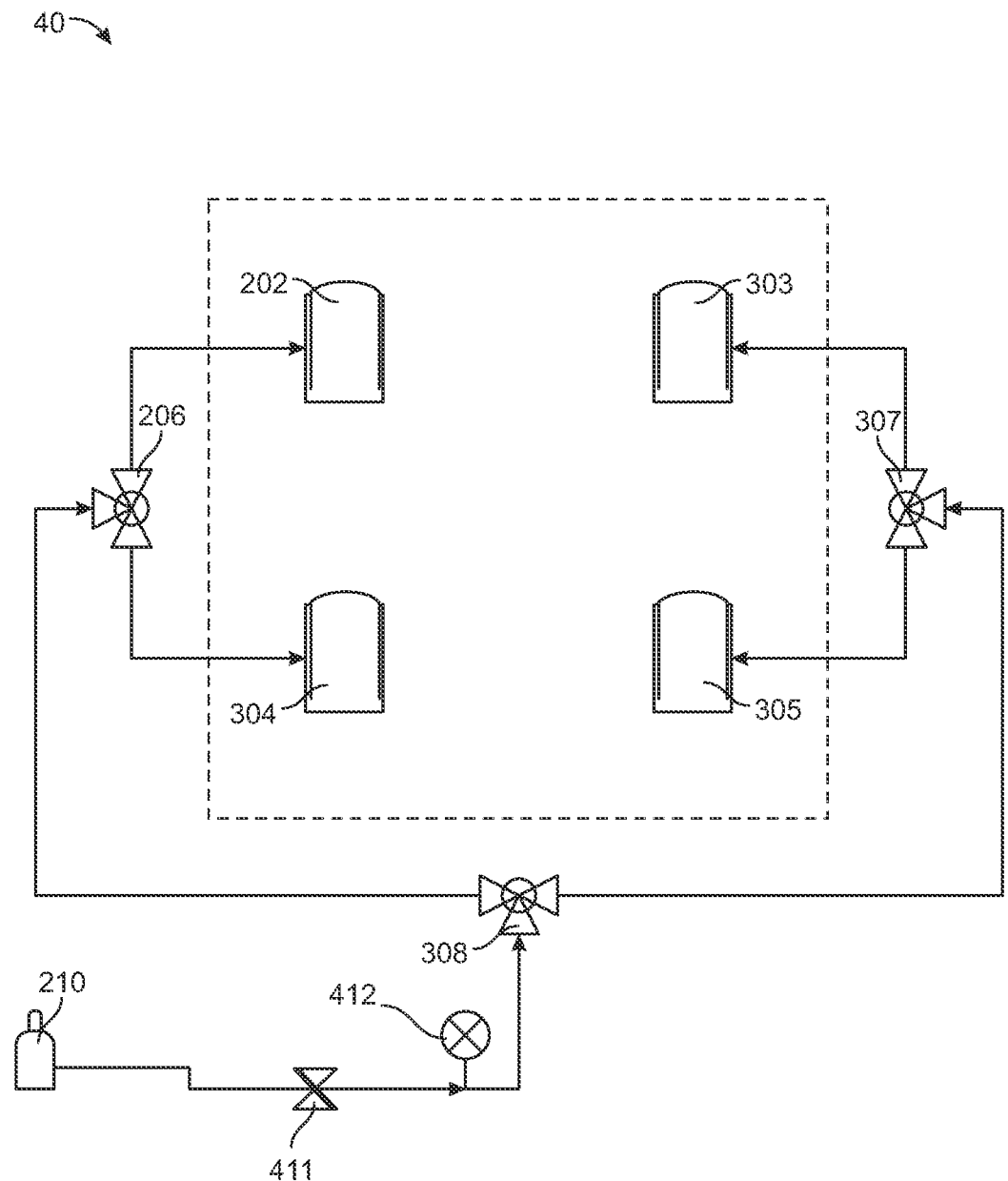
FIG. 4 shows a top schematic view of the example automated apparatus shown in FIG. 2 according to at least one embodiment of the present disclosure.

A second embodiment of an apparatus for characterizing a fluid-solid system is shown in FIGS. 3 and 4 as apparatus 30 and 40. The illustrated embodiment of FIGS. 3 and 4 is similar to that of FIG. 2, with the addition of a several more core holders (core holder 303, core holder 304, and core holder 305) and several more three-way valves (three-way valve 307 and three-way valve 308). The additional core holders and three-way valves can enable increased capacity and efficiency of the apparatus. The three-way valves can be automated.

The number of core holders and three-way valves can be any suitable number. For example, the apparatus can include from 2 to 20 core holders, such as from 2 to 10 core holders, such as from 3 to 8 core holders, 4 to 6 core holders, or any number of core holders within those ranges. Other values are contemplated. As another example, the number of three-way valves can be any suitable number, wherein the number of three-way valves in the apparatus is less than, equal to, or greater than the number of core holders. Other values are contemplated. In some examples, the apparatus includes more than one mass comparator. The number of mass comparators can be the same as the number of core holders. As described above, each adsorbent or core holder is connected to each mass comparator by, e.g., a hook or insulated wire. In this way, more than one fluid-solid system can be measured simultaneously. For example, the number of measurements carried out simultaneously can be from 1 to 20 measurements, such as from 2 to 20 measurements, such as from 2 to 10 measurements, such as from 3 to 8 measurements, such as from 4 to 6 measurements, or any number of measurements within those ranges. Higher and lower numbers of measurements are contemplated.

The apparatus further includes a check valve 411 to prevent backflow into the gas tank 210 and a pressure gauge 412 installed to monitor the pressure downstream of the check valve 411. The check valve 411 can be a one way valve or an electronic gas regulator, though other suitable check valves are contemplated. The gas tank 210 and vacuum pump 213 are independently coupled directly, or indirectly, to the three-way valve 206, the three-way valve 307, and the three-way valve 308, which are coupled to the various core holders of the apparatus. The environmental chamber control unit 215, the data acquisition and remote control unit 216, and the computer 217 are also shown. Other components are removed for clarity. In FIG. 3, electrical wire or connection is indicated by the dashed lines while gas and vacuum lines are indicated by the solid lines. In FIG. 4, gas lines are indicated by the solid lines, while the dashed box indicates the environmental chamber 207.

Figure 5:
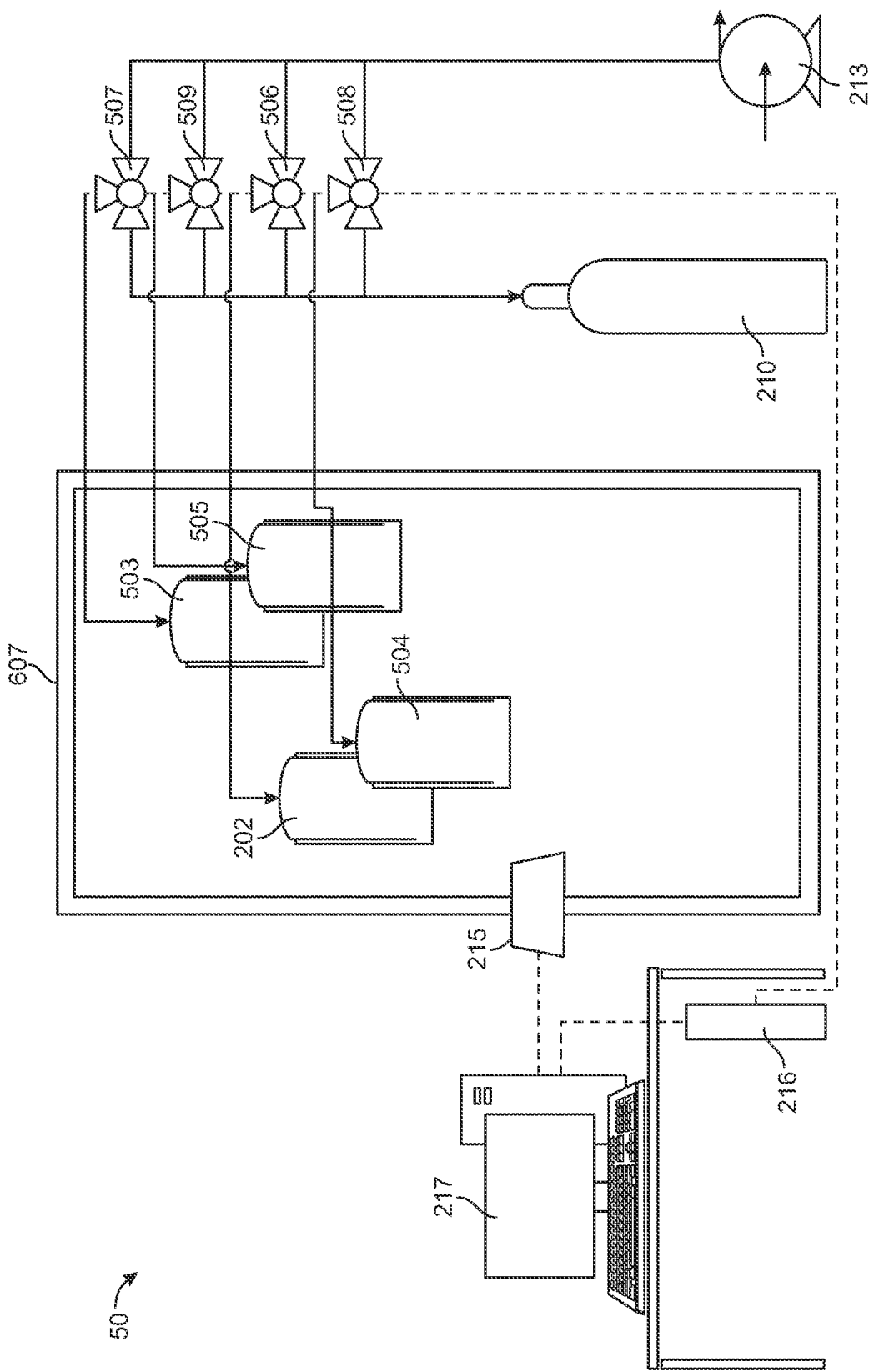
FIG. 5 shows an elevation schematic view of an example automated apparatus for characterizing a fluid-solid system according to at least one embodiment of the present disclosure.

A third embodiment of an apparatus for characterizing a fluid-solid system is shown in FIGS. 5 and 6 as apparatus 30 and 40. The illustrated embodiment of FIGS. 5 and 6 includes core holders 202, 503, 504, and 505 positioned inside of an environmental chamber 607, three-way valves 506, 507, 508, and 509, and a gas chromatograph 614. The three-way valves can be automated. The additional core holders and three-way valves can enable increased capacity and efficiency of the apparatus. Individual check valves 611*a*-611*d* are also positioned between the individual three-way valves 506, 507, 508, and 509 and the individual core holders 202, 503, 504, and 505. The environmental chamber 607 can be a temperature chamber. A manifold 615 is coupled to various lines of the system. A liquid inlet 612 and a gas inlet 613 can be coupled to the gas chromatograph 614 and to the manifold 615. The liquid inlet 612 and the gas inlet 613 can be used to inject liquid or gas, respectively, into the gas chromatograph 614. As shown, the vacuum lines can be coupled to a vacuum manifold 603 and the gas lines can be coupled to a gas manifold 605. The vacuum manifold 603 and the gas manifold 605 are positioned to provide vacuum or gas to the various components of the apparatus. As shown, the gas chromatograph 614 is operably coupled or connected to the individual core holders 202, 503, 504, and 505.

The illustrated apparatus of FIGS. 5 and 6 can be used to characterize fluid-solid systems that include gas mixtures. This capability is due at least in part to each core holder 202, 503, 504, 505 having its own independent connection to the gas tank 210, vacuum pump 213, and the gas chromatograph 614. In FIG. 5, electrical wire or connection is indicated by the dashed lines while gas and vacuum lines are indicated by the solid lines. In FIG. 6, vacuum lines are indicated by solid lines and gas lines are indicated by dashed lines. The dash-dotted lines represent the flow of gas, vacuum or liquid between one or more of vacuum manifold 603, gas manifold 605, liquid inlet 612, gas inlet 613, gas chromatograph 614, or manifold 615.

As described herein, embodiments of apparatus for studying or characterizing a fluid-solid system are automated. The automated apparatus (or automated system) includes hardware and software. The software can be part of the data acquisition and remote control unit 216. The data acquisition and remote control unit 216, as part of the automated system, can perform one or more of the following operations. The one or more of the following operations can be performed automatically by the automated system to achieve the automation:

(a) The automated system accepts live data feed from the pressure gauges and mass comparators coupled to the individual core holders and analyzes the data in real time.

(b) The automated system determines if pressure stabilization has been reached and a new data point is to be recorded.

(c) The automated system records new data points taking the average of pressure and mass values over a pre-determined duration. Data points may also be customized by the user.

(d) The automated system introduces or retracts one or more fluids to prepare for a new data point measurement.

(e) The automated system allows for user intervention at any suitable point without interrupting the running experiment.

(f) The automated system allows for switching between manual mode and automated mode without interrupting the running experiment.

For the algorithm that the automated system is using, a simplified activity diagram 70 is presented in FIG. 7, with operations illustrated in more detail below. The initial hardware connection is made at operation 720.

(1)-(6): Operations 721, 722, 723, 726, 729, and 730 reflect the data acquisition system, the ability to observe the data in real-time on a PC monitor, and the ability to terminate the software completely. The operations include read device status (operation 721), read data stream (operation 722), plot data to graphical user interface (GUI) (operation 723), start data logging (operation 726), create data logging document (operation 729), and terminate program (operation 730). Numeral 731 represents an end point after terminate program (operation 730).

(7)-(9): Operations 727, 733, and 728 can enable seamless transitioning between Manual Mode (the ability to run the automated system manually) and Auto Mode (utilizing the newly implemented algorithm). These operations include switch to Manual Mode (operation 727), give user control (operation 733), and switch to Auto Mode (operation 728).

(10): At operation 736, the data functions are loaded. Once loaded, the data functions can take over the system control and the experiment flow as illustrated in the subsequent operations.

(11): Operation 738 represents the automated system waiting to log a sufficient amount of data in order to move forward with the experiment. The automated system may not be ready to move forward with the experiment on account of, for example, not enough data has been logged and/or when the pressure is not stable. Here, a determination (737) is made as to, e.g., whether enough data is logged and/or whether the pressure is stable. If enough data is logged and/or the pressure is stable, the experiment can proceed. If not enough data is logged and/or the pressure is not stable, the automated system waits to log a sufficient amount of data and/or stabilize the pressure at operation 738. Waiting for stabilization can take a period of about 10 minutes, though shorter or longer durations are contemplated.

(12): Operation 739 represents the core of the algorithm decision-making process. Here, the automated system takes the logged data and processes it to statistically decide if, e.g., the pressure, has stabilized and the experiment can move forward to the next pressure point. During or after operation 739, a determination (740) is made as to, e.g., whether the pressure is stabilized and/or whether enough data is logged. The determination 740 can be similar to the determination (737).

(13): Operation 741 reflects the automation of the valve opening/closing mechanism for changing pressure. The valve-opening duration (the time for which the valves are opened) may be dynamically calculated by the algorithm or manually set/changed by the user at any time. In some embodiments, the pressure is only changed when the automated system is stable. Operations 736, 738, 739, and 741 are repeated for each pressure point until the end of the experiment.

(14): Operation 742 is activated when the user stops Auto Mode and/or switches to Manual Mode, where the automated system is manually operated, thereby terminating the computer algorithm. The program terminates upon completion of the experiment.

Figure 7:
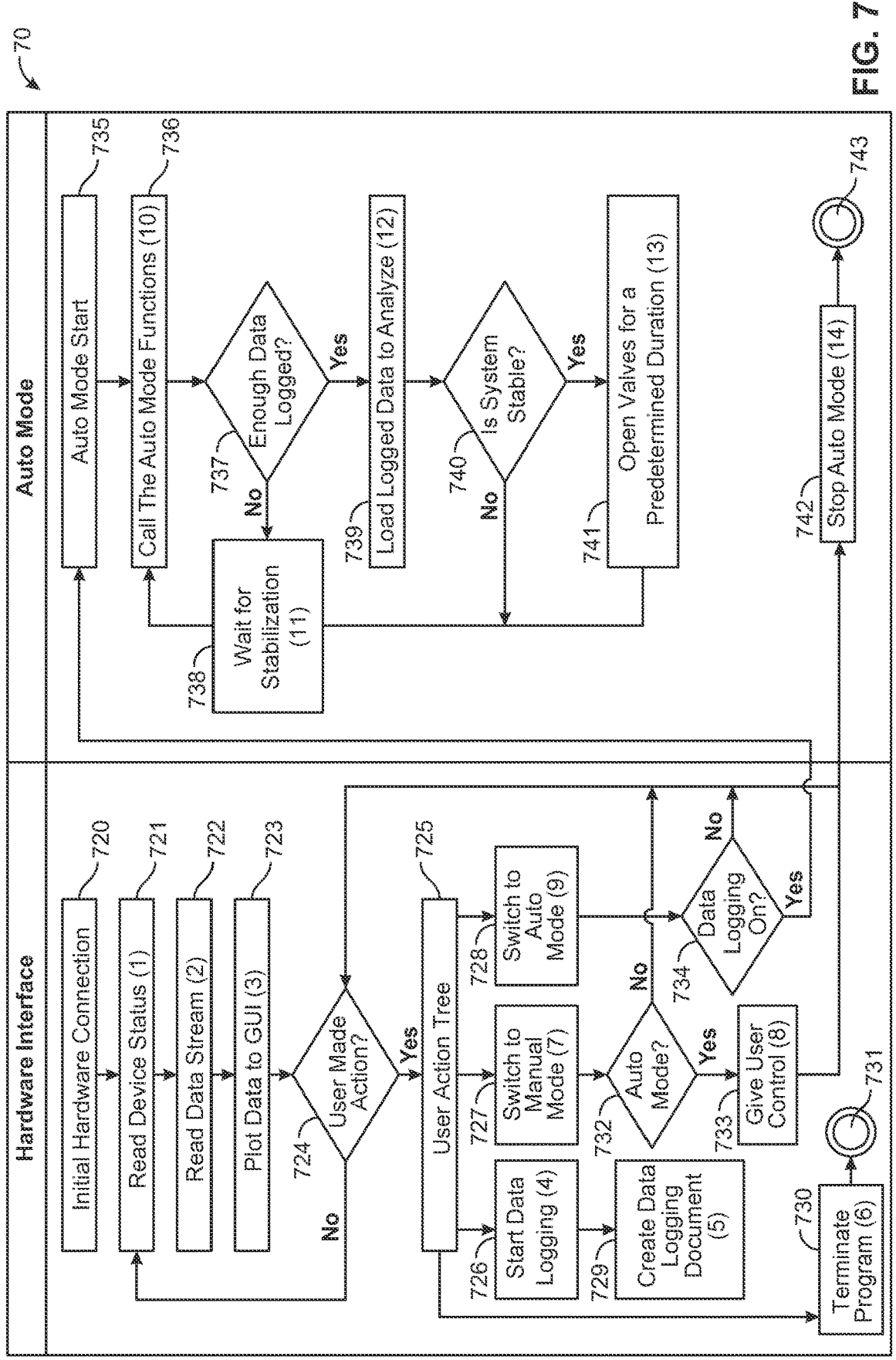
FIG. 7 is an example of an activity diagram for automation algorithm according to at least one embodiment of the present disclosure.

As shown in the simplified activity diagram 70 of FIG. 7, various determinations can be made. For example, and in some embodiments, when a user made action 724 is present, the user has an action tree 725 where various options can be chosen including switch to manual mode at operation 727 and switch to Auto Mode at operation 728, among other actions such as terminate program at operation 730. If the user made action is not present, and in at least one embodiment, operations 721-723 can be continued. As another example, an in some embodiments, after the switch to Manual Mode at operation 727, a switch to Auto Mode 732 can be present. If present, the user can be given control at operation 733. If the switch to Auto Mode 732 is not present, a determination as to user made action 724 continues until a condition is satisfied. As another example, after the switch to Auto Mode at operation 728, the user can stop Auto Mode at operation 742 by, e.g., switching to Manual Mode. If not, a determination as to user made action 724 continues until a condition is satisfied.

Further, and in some embodiments, and after a switch to Auto Mode at operation 728, a determination as to data logging on (734) is made. If yes, and in at least one embodiment, Auto Mode can start (735). If not, a determination as to user made action 724 continues until a condition is satisfied. Other determinations can be made, such as determination (737) and determination (740) described above.

In one embodiment, the algorithm of operation (739) includes an algorithm configured to solve two or more problems related to controlling the apparatus. The first problem of the two or more problems is to determine stationarity of the system at a given data point before logging that data point and moving on to the next data point. The second problem of the two or more problems is to determine the optimal duration of time to open a valve, wherein the valve separates the core holder from a vacuum line or a pressure source, in order to step the pressure up or down to the appropriate predetermined pressure set point.

Before a data point can be logged, stationarity of a time series of the pressure data is verified. Once verified, the data point can be logged and the automated system may proceed to modulate the pressure in the core holder to the next predetermined pressure set point. In some embodiments, two parallel tests can be employed to verify stationarity of the time series of pressure data corresponding to the pressure inside the core holder. The two parallel tests can be an Augmented Dickey-Fuller (ADF) test and a Kwiatkowski-Phillips-Schmidt-Shin (KPSS) test, though other tests are contemplated. A single test, two tests, or more tests can be performed.

In some embodiments, the ADF test can be used to test a null hypothesis that a unit root is present in the time series of pressure data. The alternative hypothesis of the test is that stationarity is present in the data. The ADF test is an augmented version of the Dickey-Fuller test to cover more complicated set of time series models.

The KPSS test can be used to complement the ADF test. In some embodiments, the KPSS test determines if a time series is stationary around a mean or linear trend, or is non-stationary due to existence of a unit root. The KPSS test can be used to test a null hypothesis that the data is stationary. The alternate hypothesis for the test is that the data is not stationary.

In some embodiments, the output from the ADF test is a negative number. The more negative it is, the stronger the rejection of the hypothesis that there is a unit root at some level of confidence and hence the data is stationary.

As stated above, the algorithm solves a second problem. The second problem is to determine the duration (e.g., period or interval) to open the valve to reach the desired next pressure point. Here, the valve can be a three-way valve (which may be pneumatic), such as one or more of the three-way valves (e.g., three-way valve 206) described herein. The duration (e.g., period or interval) can be on the order of milliseconds. For the second problem, generally, multiple short pulses of opening the automated valve can be performed, and data is collected and analyzed with Curve Analysis techniques to estimate or determine the next pressure point being reached. By comparing the actual target pressure point and the current pressure point being reached (due to the short pulses), one can adjust the next pulse to be, e.g., at or near a target pressure point.

Accordingly, and in some embodiments, once stationarity has been verified (first problem), the automated system may adjust the pressure inside the core holder to move to the next predetermined pressure set point by opening an automated valve (e.g., one or more of the three-way valves described herein such as three-way valve 206). In some embodiments, opening the automated valve allows compressed gas to rush into the core holder. In at least one embodiment, opening the automated valve can allow a vacuum pump to draw down the pressure inside the core holder. To reach the next pressure set point without overshooting, a predictive control scheme may be implemented. In some embodiments, in order to generate data upon which to base a prediction, the automated system executes multiple very short pulses (short intervals of opening the automated valve) and collects a short stream of data corresponding to the multiple short pulses. The shot stream of data may be analyzed via Curve Analysis techniques to estimate the period the automated valve should remain open in order to reach the next set point without too much overshoot.

The method can be performed with any apparatus described herein. The methods described herein enable quicker and more accurate data collection. For example, conventional data acquisition is at least four times slower and with much lower accuracy/resolution.

Figure 8:
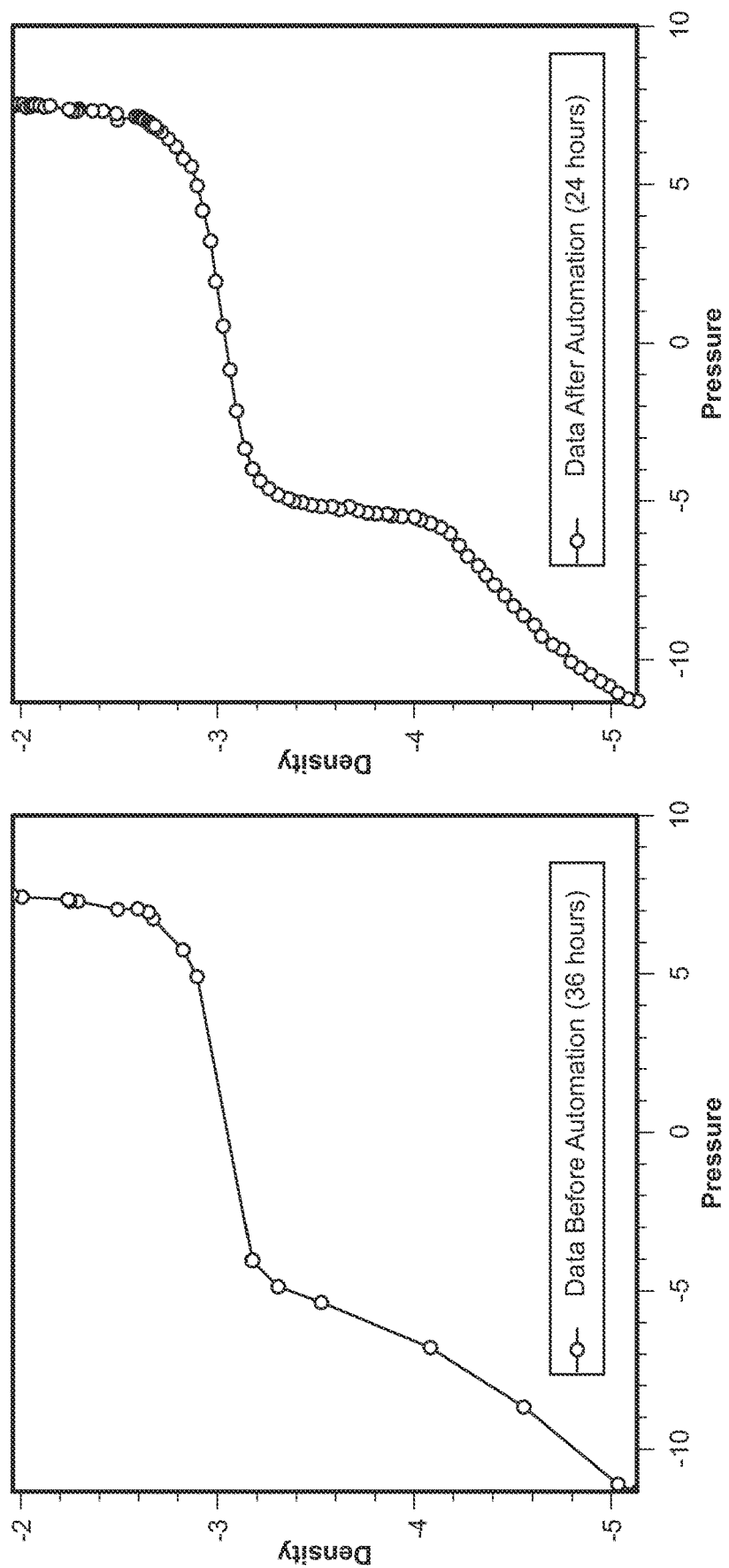
FIG. 8 is a plot showing increased data resolution and time efficiency achieved via an example automated apparatus (right panel) versus a plot using a non-automated apparatus (left panel).

The described automation of the system allows for experiments requiring less time to conduct, while improving the resolution (e.g., the number of data points collected). FIG. 8 shows the difference before (left panel) and after (right panel) the implementation of the described automation system. As shown, only about 15 or 16 data points are collected over 36 hours using conventional apparatus (left panel of FIG. 8). In contrast, and in some embodiments, more than 80 data points can be collected using the automation system described herein. Moreover, the more than 80 data points are collected in much less time (24 hours) than the conventional apparatus. Overall, FIG. 8 illustrates the increased data resolution and time efficiency achieved using embodiments of the automated apparatus described herein.

Although the described automation may be used for the generation of thermodynamic isotherms, as can be appreciated, the algorithm and system configuration may be used to study a wide range of other systems utilizing pressure-dependent data and performing actions based on pressure stabilization.

Embodiments described herein also relate to methods of characterizing or studying a fluid-solid system. The methods can be performed with apparatus described herein. Although one or more operations of a method are described with respect to the apparatus of FIG. 2, one or more operations of a method can be used with other apparatus described herein, such as the apparatus of FIGS. 1-6. Moreover, and as described above, parts or components of the apparatus in each of FIGS. 1-6 can be suitably used with one or more other apparatus described herein.

In operation, the apparatus can be utilized to study or characterize fluid-solid systems. Generally, and in some embodiments, a method of studying or characterizing a fluid-solid system includes disposing an adsorbent in a core holder, setting a temperature and/or pressure, and measuring changes in the mass of the fluid. Here, after the adsorbent is placed in the core holder, changes in the mass of a fluid present in the adsorbent can be measured with the mass comparator at various temperatures and pressures. Automation, of various operations of the methods, can be performed as described herein.

As described herein, one or more fluid-solid systems can be measured simultaneously if desired, using various fluids, adsorbents, and/or operating parameters. Here, an individual fluid-solid system can be measured in an individual core holder. The number of mass comparators can be equal to the number of core holders.

In some embodiments, a method of characterizing or studying a fluid-solid system is provided. To begin, a porous rock sample is disposed or placed in a core holder (e.g., core holder 202). The method further includes (a) contacting or introducing the porous rock sample with a fluid to create the fluid-solid system inside the core holder. The method can further include (b) automatically adjusting a temperature and/or pressure of the fluid-solid system to a preselected value via a processor and at least one automated valve (e.g., three-way valve 206). The method can further include: (c) monitoring the fluid-solid system for equilibrium; (d) recording a value for temperature, pressure, and/or mass of the fluid solid system, to provide recorded data. The method can further include (e) performing an action based on the recorded data. The method can further include (f) repeating one or more of these operations, as desired. For example, the automatically adjusting a temperature and/or pressure of the fluid-solid system, monitoring the fluid-solid system for equilibrium, performing an action based on the recorded data, and/or recording operation can be repeated. In some examples, the data can be acquired and operations of the method can be controlled by, e.g., data acquisition and remote control unit 216. The data acquisition and remote control unit 216 can perform one or more operations of the method. As described above, the data acquisition and remote control unit 216 includes one or more processors configured to perform various operations of the method.

The operation of (e) performing an action can include analyzing a pressure signal for stationarity. The pressure signal analyzed for stationarity can correspond to the pressure within the core holder. An ADF test and/or a KPSS test can be performed during analyzing a pressure signal for stationarity. The pressure signal corresponds to the pressure within the core holder 202. In at least one embodiment, the fluid-solid system is monitored for equilibrium via a pressure sensor or pressure transducer, e.g., pressure transducer (j).

In some embodiments of the method, the at least one automated valve (e.g., three-way valve 206) can be a pressure control valve. In these and other embodiments the operation of (e) performing an action can include opening the pressure control valve (e.g., three-way valve 206) for a calculated period of time. In at least one embodiment, the operation of (e) performing an action can include opening the pressure control valve (e.g., three-way valve 206) for a calculated period of time can include performing a series of short valve openings in order to generate a series of data, and analyzing the series of data in order to calculate the calculated period of time. In some embodiments, the operation of (e) performing an action can include adjusting the pressure of the fluid-solid system.

The operation of (e) performing an action, in some embodiments, can optionally include introducing or injecting additional fluid into the core holder (e.g., core holder 202). The fluid can be the same fluid or a different fluid. The additional fluid can be introduced or injected into the core holder 202 by opening an automated valve (e.g., three-way valve 206) for a predetermined duration of time, via the one or more processors. During introducing or injecting the additional fluid, the automated valve (e.g., three-way valve 206) is in fluid communication with a source of pressure. The source of pressure can include a vessel of compressed gas (e.g., gas tank 210).

In at least one embodiment, the operation of (e) performing an action can optionally include removing at least some fluid from the core holder 202. Removing at least some fluid from the core holder 202 can include opening an automated valve (e.g., three-way valve 206) for a predetermined duration of time, via the one or more processors. During removing at least some of the fluid, the automated valve (e.g., three-way valve 206) is in fluid communication with a source of vacuum (e.g., vacuum pump 213).

In some examples, the operation of (e) performing an action includes calculating an a mean, a median, or an average of pressure values and/or a mean, a median, or an average mass values over a pre-determined time duration. Other calculations can be performed by the one or more processors. Raw data for the pressure values and/or mass values can be collected by using the data acquisition and remote control unit 216, a pressure sensor or pressure transducer, e.g., pressure transducer (j), and a mass comparator, e.g., mass comparator (a). The pressure sensor or pressure transducer (j) is coupled to, or operationally connected to, an interior of the core holder 202. The pressure sensor or pressure transducer (j) is configured to sense a pressure within the core holder and produce a pressure signal. The mass comparator (a) is coupled to, or operationally connected to, an interior of the core holder 202. The pressure sensor or pressure transducer (j) and the mass comparator are each, individually, coupled to, or operationally connected to, the data acquisition and remote control unit 216.

The method of characterizing or studying a fluid-solid system can optionally include controlling the atmosphere within the environmental chamber (e.g., environmental chamber 207) via an automated purge valve. As described above, an atmospheric purge mechanism is configured to purge the interior of the environmental chamber 207 of materials, e.g., oxygen. The automated purge mechanism includes an automated purge valve. The automated purge valve can be positioned between the source of non-reactive gas and the environmental chamber 207, and can be configured to control a flow of the non-reactive gas into the environmental chamber 207. In these and other embodiments, the automated purge valve is in selective fluid communication with a source of non-reactive gas. Controlling the atmosphere within the environmental chamber (e.g., environmental chamber 207) via an automated purge valve can be part of the operation of (e) performing an action, or a different operation.

In some embodiments, methods described herein further include automatically interpreting, transforming, and/or recording unprocessed signals from a pressure sensor, a temperature sensor, and a mass comparator (among other sensors) into a thermodynamic data characteristic, e.g., an isotherm, of the fluid-solid system.

Adsorbents that can be studied and characterized using apparatus, systems, and methods described herein include, but are not limited to, one or more ideal adsorbents, one or more reservoir cores, or combinations thereof. As used herein, the term "ideal adsorbent" refers to an ordered nanoporous material. As used herein, the term "reservoir core" refers to a sample of reservoir rock. Reservoir rock is a type of nanoporous rock that contains, e.g., oil, gas, brine, and/or $CO_2$. Ideal adsorbents and reservoir cores can be porous rock samples.

Fluids (which include a liquid, a gas, or a combination thereof) that can be utilized for the studies and characterizations described herein can include one or more simple fluids, one or more reservoir fluids, or both. As used herein, the term "simple fluid" refers to a single-component liquid or gas. Examples of simple fluids include, but are not limited to $C_1$ to $C_{20}$ alkanes (e.g., methane, ethane, propane, butane, isobutane, pentane, neopentane, hexane, heptane, octane, nonane, and decane), $C_2$ to $C_{20}$ alkenes (e.g., ethene, propene, butene, pentene, hexene, heptene, octene, nonene, decene), $C_2$ to $C_{20}$ alkynes, $C_1$ to $C_{20}$ alkanols (e.g., methanol, ethanol, isopropanol), $C_2$-$C_{20}$ alkenols, aromatic hydrocarbons (e.g., benzene, toluene), $C_3$-$C_{20}$ cycloalkanes (e.g., cyclopentane, cyclohexane, methylcyclohexane), $C_3$-$C_{20}$ cycloalkenes, water, nitrogen, carbon dioxide, and oxygen. Isomers of these aforementioned fluids are also contemplated. For example, reference to butane expressly discloses n-butane, iso-butane, etc. As used herein, the term "reservoir fluid" refers to a fluid mixture found in a reservoir rock.

Methods of studying or characterizing a fluid-solid system can include performing operations at various temperature and pressure conditions, such as ambient temperature and pressure conditions, reservoir temperature and pressure conditions, or combinations thereof, among other temperature and pressure conditions. As used herein, the term "reservoir temperature and pressure conditions" refers to conditions wherein the temperature and pressure reflect the temperature and pressure of reservoir rock. The temperature and pressure of the reservoir rock varies as a function of the reservoir rock's proximity to the earth's mantle and the composition of the porous medium of the reservoir rock. Reservoir temperatures and pressures can be determined by methods known in the art. As used herein, the term "ambient temperature and pressure conditions" refers to conditions wherein the temperature is about room temperature and the pressure is about atmospheric pressure. Room temperature ranges from about 15° C. to about 30° C., such as from about 18° C. to about 27° C., such as from about 20° C. to about 25° C. Atmospheric pressure ranges from about 750 mbar (~0.74 atm) to about 1050 mbar (~1.03 atm), such as about 1013 mbar (~1 atm). As used herein, the term "vacuum" refers to reduced pressures in the range of about $10^{-12}$ mbar to about 750 mbar.

Methods of studying or characterizing a fluid-solid system can include injecting one or more fluids continuously and/or stepwise into the adsorbent. The one or more fluids can be injected with a pump and/or by hand. Methods of studying or characterizing a fluid-solid system can include adjusting and/or measuring the temperature, pressure, or both of the apparatus. The temperature can be measured by using, e.g., a thermocouple. The pressure can be measured using, e.g., a pressure sensor or pressure transducer.

Methods of studying or characterizing a fluid-solid system can include measuring a mass of the fluid and/or a pressure of the fluid. The mass and/or pressure of the fluid can be measured over an equilibrium time, continuously or at selected time intervals. The equilibrium time can be a range of about 0.1 seconds (s) to about 20,000 s, such as from about 0.5 s to about 10,000 s, such as from about 1 s to about 5,000 s, though shorter or longer times are contemplated. The selected time intervals, in some embodiments, can be averaged over a range of about 0.1 s to about 100 s, such as from about 0.5 s to about 50 s, such as from about 1 s to about 10 s. In some embodiments, the pressures and/or masses of the fluid measured at the selected time intervals can be averaged over the equilibrium time.

Embodiments of the present disclosure can be further understood by the following non-limiting examples. The following examples are put forth so as to provide those of ordinary skill in the art with a complete disclosure and description of how to make and use aspects of the present disclosure, and are not intended to limit the scope of aspects of the present disclosure.

EXAMPLES

Use of the Apparatus. The systems are leak tested to ensure, e.g., none of the permanent metal tubing leaks under pressure or vacuum. The tubing was tested under pressure first, then under vacuum. Installation of the core holder included: (1) connecting the core holder to the rest of the nanocondensation apparatus, (2) leak testing the core holder, and (3) outgassing the system. Other installation schemes are contemplated.

An example isothermal capillary condensation experiment is presented below in Example 1. Certain operations of Example 1 can be automated as described herein.

Example 1. Isothermal capillary condensation experiment. The software for Auto Mode is begun. The core holder is first filled with an adsorbent sample and hung inside the environmental chamber from a hook or insulated wire on the bottom of the mass comparator via an insulated wire. Next, the core holder and tubing of the apparatus is subjected to high vacuum and a temperature of approximately 100° C. to degas any vapors in the system. Once degassing is finished, the temperature of the environmental chamber is set to a desired experimental temperature ("$T_{exp}$"). To study fluid adsorption, a fluid is injected into the core holder at a desired experimental pressure ("$P_1$") by a pump such as a Quizix pump. Constant temperature and pressure are maintained until fluid adsorption is complete (e.g., until no changes in the mass or the pressure of the fluid are observed). Several adsorption measurements can be taken in sequence. Alternatively, an adsorption measurement can be taken, and, once adsorption is complete, a desorption measurement can be taken. To study fluid desorption, the mass and pressure of the adsorbed fluid are measured. Constant temperature and pressure are maintained until desorption of the fluid is complete (e.g., until no changes in the mass or the pressure of the fluid are observed). Once desorption was finished, the temperature of the environmental chamber is set to $T_{exp}$ again, the pressure was increased to a new desired pressure ("$P_2$"), and the fluid was injected again until adsorption was complete. Several desorption measurements can be taken in sequence. Alternatively, a desorption measurement can be taken, and, once desorption is complete, an adsorption measurement can be taken. These adsorption and desorption steps are repeated, at constant temperature and different pressures, as many times as desired. In particular, the adsorption and desorption steps are repeated until a full adsorption isotherm (e.g., a plot of fluid amount adsorbed against pressure) is created. Completion of adsorption can be evidenced by constant mass and pressure readings for an extended period of time. Similarly, completion of desorption can be evidenced by constant mass and pressure readings for an extended period of time. Mass readings are taken from the mass comparator, and pressure readings are taken from pressure transducers or vacuum gauges that are located outside of the environmental chamber.

In the following examples, isotherms were generated were generated by recording the pressure and mass readings in real time from the gravimetric adsorption apparatus. Isotherms for n-butane and iso-butane were measured. MCM-41 was used as an example adsorbent in some examples.

Figure 9:
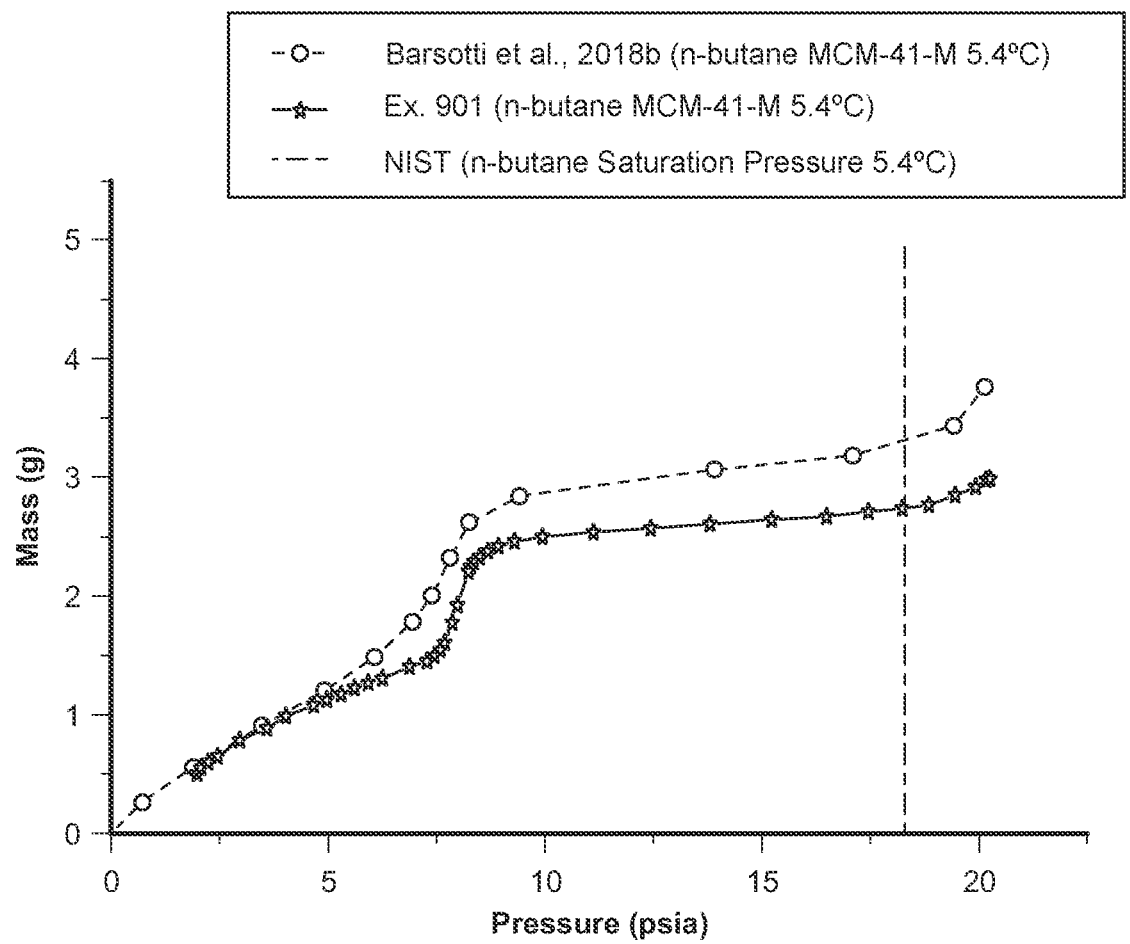
FIG. 9 shows a comparison of a previously published n-butane adsorption isotherm at 5.4° C. overlaid with an n-butane adsorption isotherm at the same conditions produced via an example automated apparatus according to at least one embodiment of the present disclosure.

Example 2. An automated apparatus described herein was validated by reproducing a known published isotherm at the same conditions, namely n-butane at about 5.4° C. The automated apparatus was validated against published data from the National Institute of Standards and Technology (NIST) using the saturation pressure of about 18.284 psia. The results are shown in FIG. 9. As can be seen, the newly generated isotherm (labeled as Ex. 901) and the previously established isotherm (labeled as Barsotti et al., 2018b) match in all general characteristics, including condensation pressure and bulk pressure. The difference along the y-axis is attributed to a difference in the amounts of adsorbent (MCM-41) and does not affect calculating the condensation pressure from the isotherm.

Figure 10:
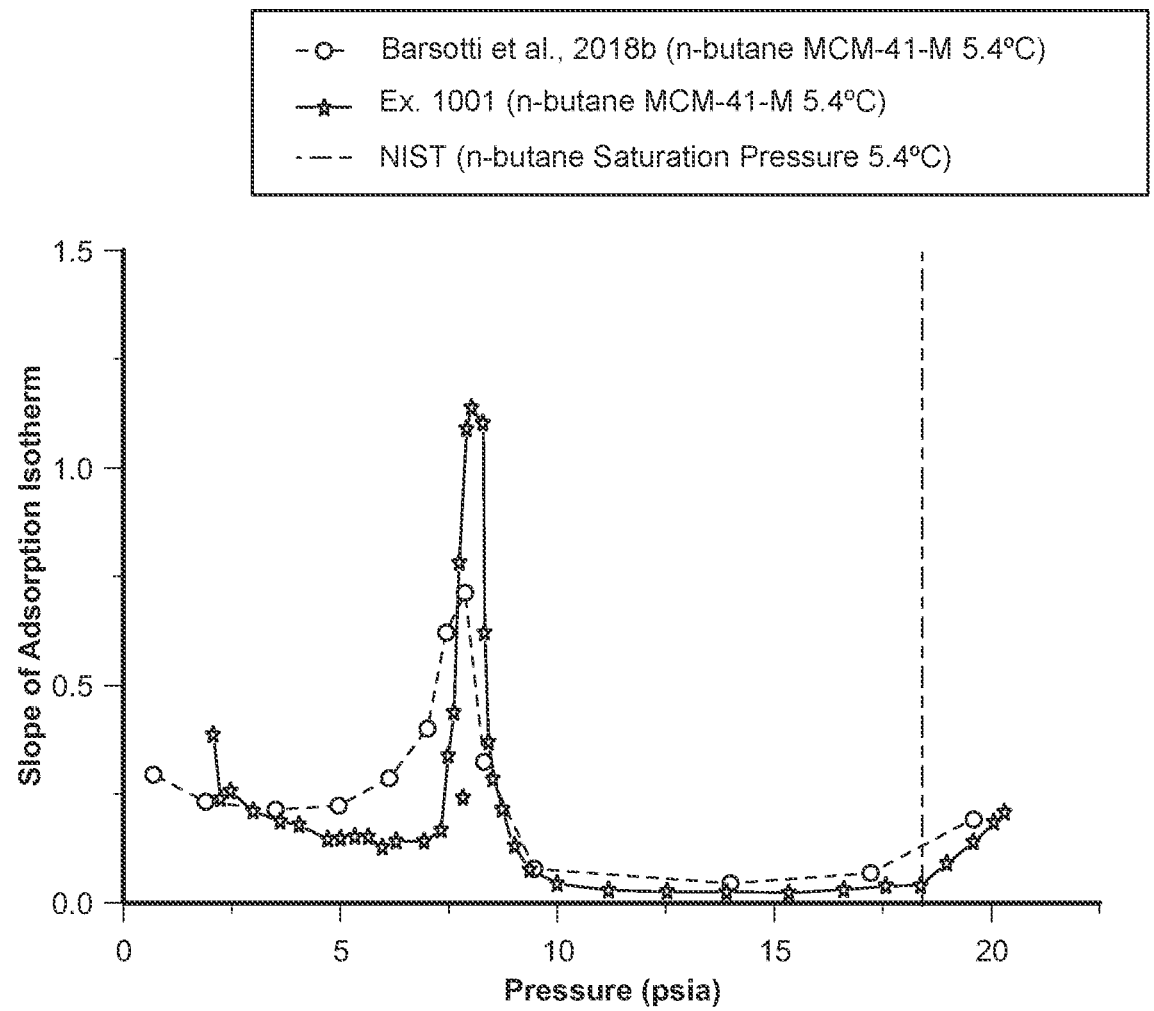
FIG. 10 shows a comparison of previously published slope of adsorption isotherm vs pressure of n-butane at 5.4C data set overlaid with a similar dataset produced via an example automated apparatus according to at least one embodiment of the present disclosure.

FIG. 10 shows a comparison shows a comparison of previously published slope of adsorption isotherm vs pressure of n-butane at 5.4C data set overlaid with a similar dataset produced via an example automated apparatus of the present disclosure. The previously published data is labeled as Barsotti et al., 2018b, and the newly generated data using an example automated apparatus is labeled as Ex. 1001. As can be seen, the isotherm generated via the automated apparatus (Ex. 1001) has a significantly higher resolution isotherm, e.g., more data points. This increase in resolution/data points directly translates into, e.g., more precise calculation of the condensation/evaporation pressures derived from the adsorption/desorption isotherms, respectively. In addition, the higher resolution at the end of the isotherm can allow for better matching with the data from the NIST and hence better correction for any experimental errors, if any.

Besides the higher resolution and accuracy afforded by the automated apparatus described herein, the total time to perform the experiment and generate isotherms can be reduced or made more efficient. For example, because the apparatus is automated, the apparatus can work round the clock, and may generate high-resolution isotherms in less than 48 hours.

Figures 11A, 11B:
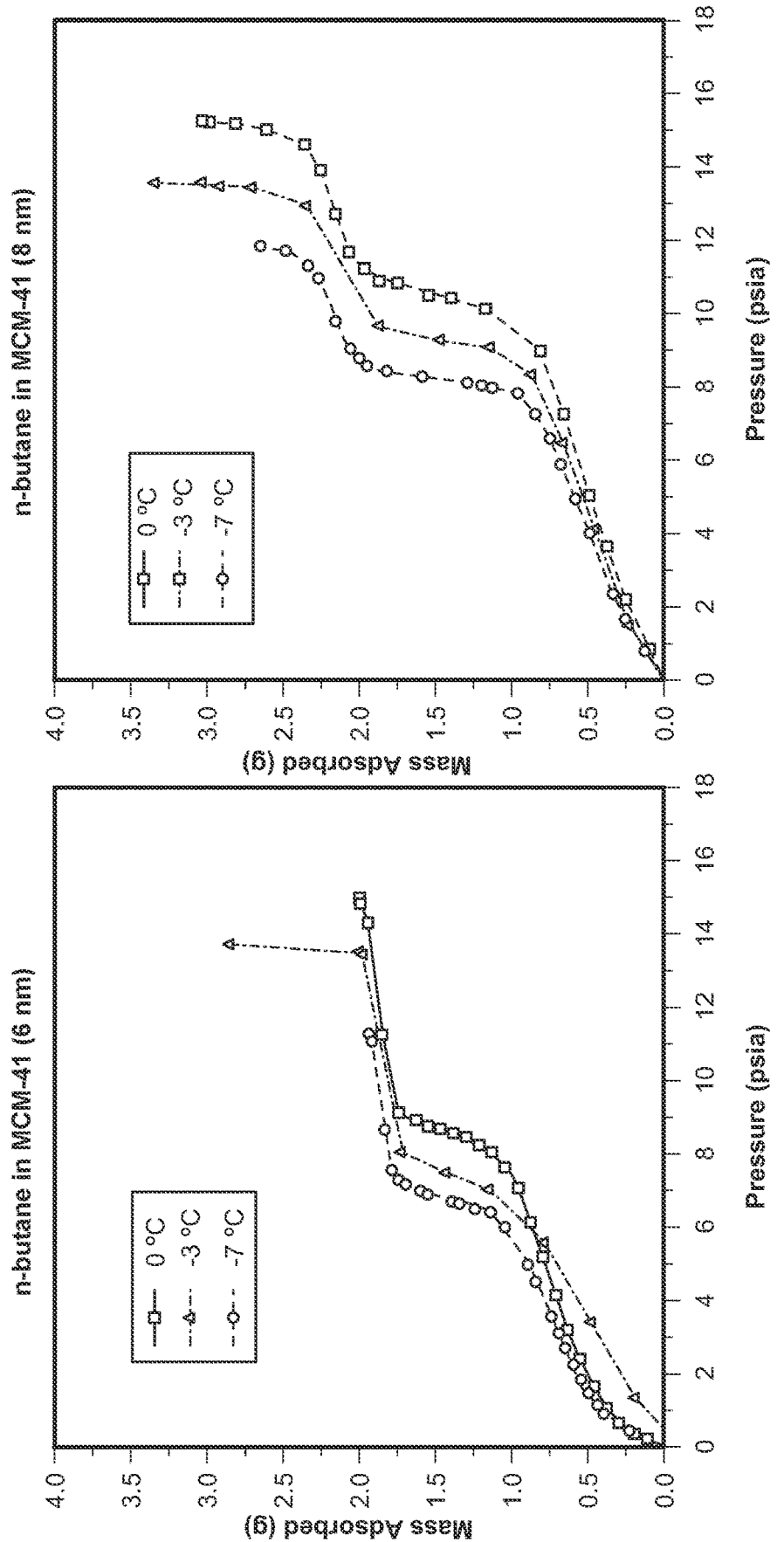
FIG. 11A shows isotherm data for n-butane in MCM-41 (pore size of 6 nm) at different temperatures produced via an example automated apparatus according to at least one embodiment of the present disclosure.
FIG. 11B shows isotherm data for n-butane in MCM-41 (pore size of 8 nm) at different temperatures produced via an example automated apparatus according to at least one embodiment of the present disclosure.

Example 3. The ability of the automated apparatus described herein to regenerate existing datasets was demonstrated in Example 2 (above). In Example 3, the ability of the automated apparatus to generate new isotherms for new pore sizes and temperatures is demonstrated. FIGS. 11A and 11B shows the new/non-reported isotherms of n-butane at different temperatures (0° C., −3° C., and −7° C.) using MCM-41 as an adsorbent. The MCM-41 tested had different pore sizes of 6 nm (FIG. 11A) and 8 nm (FIG. 11B). The data indicates that the automated apparatus described herein provides, e.g., higher resolution isotherms and short overall experiment time relative to conventional apparatus. The data also indicates that the automated apparatus can generate datasets for new conditions.

Figure 12:
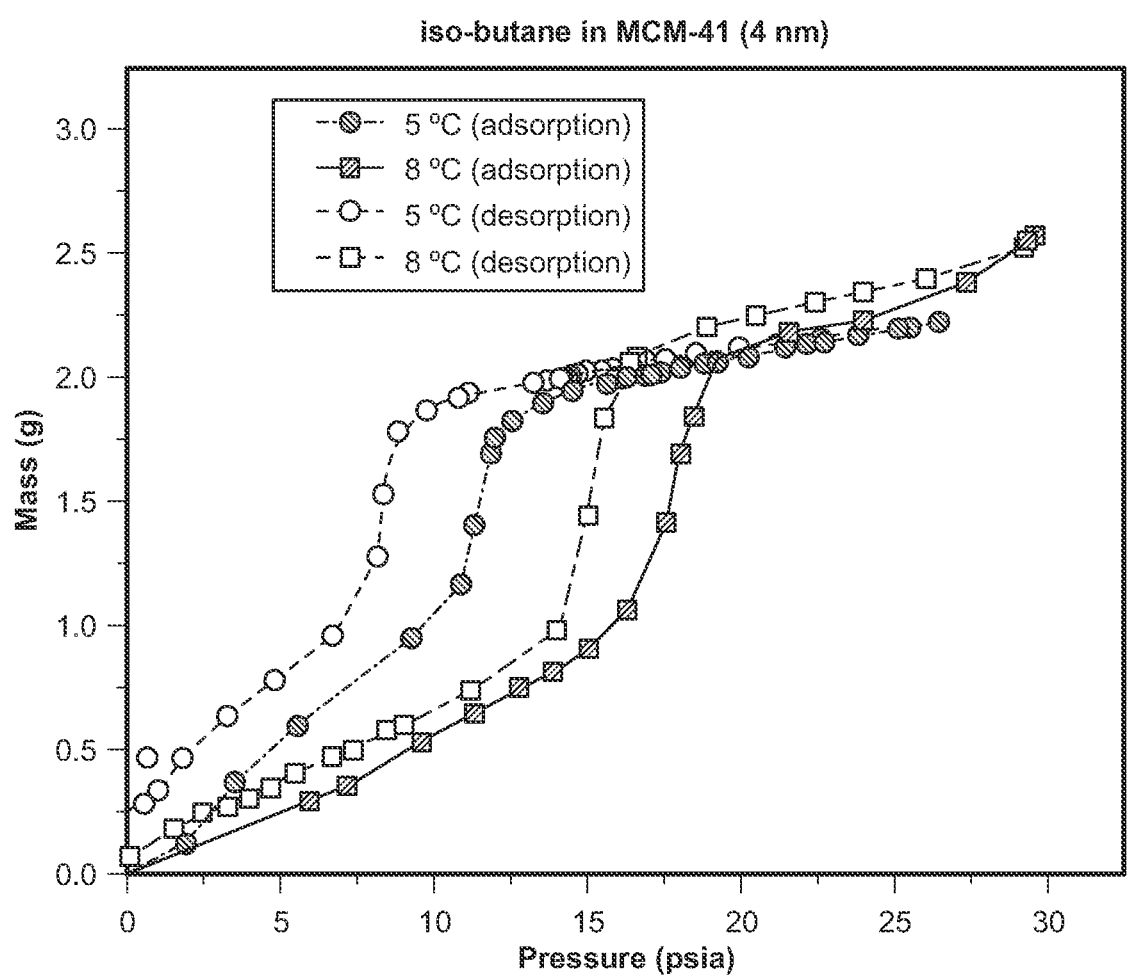
FIG. 12 shows isotherm data for iso-butane in MCM-41 at two different temperatures produced via an example automated apparatus according to at least one embodiment of the present disclosure.

Example 4. FIG. 12 shows isotherm data for iso-butane in MCM-41 (pore size of 4 nm) at two different temperatures—5° C. and 8° C.—produced via an example automated apparatus of the present disclosure. Adsorption and desorption data were determined. The four isotherms illustrate the ability of the new automated apparatus described herein to generate new datasets for new components not previously published.

Embodiments described herein generally relate to apparatus, systems, and methods for studying interactions between fluids and solids and for characterizing fluid-solid systems. Overall, the results illustrated that the embodiments described herein can allow for reduced experiment time while improving the resolution of the data. Further, numerous experiments can be conducted simultaneously at, e.g., ambient conditions, reservoir conditions, or other conditions Embodiments Listing The present disclosure provides, among others, the following embodiments, each of which can be considered as optionally including any alternate embodiments:

Clause 1. An apparatus for characterizing a fluid-solid system, the apparatus comprising:
- a core holder;
- a pressure sensor coupled to the core holder, the pressure sensor configured to sense a pressure within the core holder and produce a pressure signal;
- a mass comparator operationally connected to an interior of the core holder; and
- a pressure and flow control system comprising:
  - a pressure source in selective fluid communication with the core holder;
  - an automated pressure valve configured to control pressure within the core holder; and
  - a processor configured to:
    - control the automated pressure valve based at least in part on the pressure signal; and
    - log data from the pressure sensor and the mass comparator.

Clause 2. The apparatus of Clause 1, wherein the processor is further configured to step the pressure within the core holder through a series of predetermined pressure set points.

Clause 3. The apparatus of Clause 2, wherein the processor is further configured to:
- control the pressure within the core holder to a first predetermined pressure set point;
- analyze the pressure signal for stationarity; and
- open the automated pressure valve for a calculated period of time to control the pressure within the core holder to a second predetermined pressure set point.

Clause 4. The apparatus of Clause 3, wherein the processor is further configured to analyze the pressure signal for stationarity by an Augmented Dickey-Fuller (ADF) test and/or a Kwiatkowski-Phillips-Schmidt-Shin (KPSS) test.

Clause 5. The apparatus of Clause 3 or Clause 4, wherein the processor is further configured to calculate the calculated period of time by:
- performing a series of short valve openings in order to generate a series of data; and
- analyzing the series of data in order to calculate the calculated period of time.

Clause 6. The apparatus of any one of Clauses 1-5, further comprising:
- a vacuum source in selective fluid communication with the core holder; and
- an automated vacuum valve configured to control pressure within the core holder, wherein the processor is further configured to control the automated vacuum valve.

Clause 7. The apparatus of any one of Clauses 1-6, wherein:
- the core holder is disposed inside an environmental chamber, the environmental chamber comprising:
- a heating element, a cooling element, or both; and
- a temperature sensor; and
- the processor is further configured to control a temperature within the environmental chamber.

Clause 8. The apparatus of any one of Clauses 1-7, further comprising a gas chromatograph operably connected to the core holder, wherein the processor is further configured to automatically direct contents of the core holder into the gas chromatograph.

Clause 9. The apparatus of any one of Clauses 1-8, wherein the processor is further configured to automatically log data from the pressure sensor and the mass comparator.

Clause 10. The apparatus of any one of Clauses 1-9, wherein the core holder is a first core holder, the apparatus further comprising at least a second core holder.

Clause 11. A method of characterizing a fluid-solid system, the method comprising:
- (a) contacting a porous rock sample, disposed within a core holder, with a fluid to form a fluid-solid system inside the core holder;
- (b) automatically adjusting a temperature of the fluid-solid system, a pressure of the fluid-solid system, or both, to a preselected value via a processor and at least one automated valve;
- (c) monitoring the fluid-solid system for equilibrium;
- (d) recording a value for temperature, a value for pressure, a value for mass, or a combination thereof, of the fluid-solid system, to provide recorded data;
- (e) performing an action based on the recorded data; and
- (f) repeating one or more of operations (b) through (e) to produce a thermodynamic data characteristic of the fluid-solid system.

Clause 12. The method of Clause 11, wherein:
- the fluid-solid system is monitored for equilibrium via a pressure sensor; and
- the performing an action operation (e) comprises analyzing a pressure signal for stationarity, the pressure signal corresponding to the pressure within the core holder, the analyzing the pressure signal for stationarity comprising performing an Augmented Dickey-Fuller (ADF) test, a Kwiatkowski-Phillips-Schmidt-Shin (KPSS) test, or both.

Clause 13. The method of Clause 11 or Clause 12, wherein:
- the at least one automated valve is a pressure control valve; and
- the performing an action operation (e) comprises opening the pressure control valve for a calculated period of time.

Clause 14. The method of Clause 13, wherein the performing an action operation (e) comprises:
- performing a series of short valve openings in order to generate a series of data; and
- analyzing the series of data in order to calculate the calculated period of time.

Clause 15. The method of any one of Clauses 11-14, wherein the performing an action operation (e) comprises calculating an average of pressure values, an average of mass values, or both, over a pre-determined time duration.

Clause 16. The method of any one of Clauses 11-15, wherein the performing an action operation (e) comprises adjusting the pressure of the fluid-solid system, the adjusting the pressure of the fluid-solid system comprising:
 introducing additional fluid into the core holder;
 removing at least some fluid from the core holder; or
 a combination thereof.

Clause 17. The method of Clause 16, wherein:
 when the performing an action operation (e) comprises introducing additional fluid into the core holder, introducing additional fluid into the core holder comprises opening an automated valve for a predetermined duration of time, via the processor, the automated valve being in fluid communication with a source of pressure; or
 when the performing an action operation (e) comprises removing at least some fluid from the core holder, removing at least some fluid from the core holder comprises opening an automated valve for a predetermined duration of time, via the processor, the automated valve being in fluid communication with a source of vacuum.

Clause 18. The method of any one of Clauses 11-17, wherein the core holder is disposed within an environmental chamber, and wherein the method further comprises controlling the atmosphere within the environmental chamber via an automated purge valve, the automated purge valve being in selective fluid communication with a source of non-reactive gas.

Clause 19. The method of any one of Clauses 11-18, further comprising automatically interpreting, transforming, and recording unprocessed signals from a pressure sensor, a temperature sensor, and a mass comparator into a thermodynamic data characteristic of the fluid-solid system.

Clause 20. A method of characterizing a fluid-solid system, comprising:
 (a) introducing a fluid with a porous rock sample disposed within a core holder to form a fluid-solid system inside the core holder;
 (b) automatically adjusting a pressure of the fluid-solid system to a preselected value via a processor and at least one automated valve, wherein the automatically adjusting comprises:
  performing a series of short valve openings in order to generate a series of data; and
  analyzing the series of data in order to calculate the calculated period of time;
 (c) monitoring the fluid-solid system for equilibrium by a pressure sensor;
 (d) recording a value for pressure, a value for mass, or a combination thereof, of the fluid-solid system, to provide recorded data; and
 (e) performing an action based on the recorded data, the performing an action comprising:
  analyzing a pressure signal for stationarity by performing an Augmented Dickey-Fuller (ADF) test, a Kwiatkowski-Phillips-Schmidt-Shin (KPSS) test, or both, the pressure signal corresponding to the pressure within the core holder;
 (f) repeating one or more of operations (b) through (e) to produce a thermodynamic data characteristic of the fluid-solid system.

Clause 21. An apparatus for characterizing a fluid-solid system, the apparatus comprising:
 an environmental chamber;
 a core holder disposed inside the environmental chamber;
 a pressure sensor configured to sense the pressure within the core holder and produce a pressure signal;
 a mass comparator operationally connected to an interior of the core holder; and
 a pressure and flow control system comprising:
  a pressure source in selective fluid communication with the core holder;
  an automated pressure valve configured to control pressure within the core holder; and
  a processor configured to control the automated pressure valve based at least in part on the pressure signal.

Clause 22. The apparatus of Clause 21, wherein the processor is further configured to step the pressure within the core holder through a series of predetermined pressure set points.

Clause 23. The apparatus of Clause 21 or Clause 22, wherein the processor is further configured to:
 control the pressure within the core holder to a first predetermined pressure set point;
 analyze the pressure signal for stationarity; and
 open the automated pressure valve for a calculated period of time to control the pressure within the core holder to a second predetermined pressure set point.

Clause 24. The apparatus of Clause 23, wherein the processor is further configured to analyze the pressure signal for stationarity by an Augmented Dickey-Fuller (ADF) test and/or a Kwiatkowski-Phillips-Schmidt-Shin (KPSS) test.

Clause 25. The apparatus of Clause 23 or Clause 24, wherein the processor is further configured to calculate the calculated period of time by:
 performing a series of short valve openings in order to generate a series of data; and
 analyzing the series of data in order to calculate the calculated period of time.

Clause 26. The apparatus of any one of Clauses 21-26, further comprising a vacuum source in selective fluid communication with the core holder.

Clause 27. The apparatus of Clause 26, further comprising an automated vacuum valve configured to control pressure within the core holder, wherein the processor is further configured to control the automated vacuum valve.

Clause 28. The apparatus of any one of Clauses 21-27, wherein the environmental chamber comprises a heating element and a temperature sensor, and wherein the processor is further configured to control the temperature within the environmental chamber.

Clause 29. The apparatus of any one of Clauses 21-28, wherein the environmental chamber comprises a cooling element.

Clause 30. The apparatus of any one of Clauses 21-29, wherein the environmental chamber comprises an atmospheric purge mechanism configured to purge an interior of the environmental chamber of oxygen.

Clause 31. The apparatus of Clause 30, further comprising:
 a source of non-reactive gas in selective fluid communication with the interior of the environmental chamber; and
 an automated purge valve configured to control a flow of the non-reactive gas into the environmental chamber, wherein the processor is further configured to control the atmosphere within the environmental chamber via the automated purge valve.

Clause 32. The apparatus of any one of Clauses 21-31, further comprising a gas chromatograph operably connected to the core holder, wherein the processor is further configured to automatically direct contents of the core holder into the gas chromatograph.

Clause 33. The apparatus of any one of Clauses 21-32, wherein the processor is further configured to automatically log data from the pressure sensor and the mass comparator.

Clause 34. The apparatus of any one of Clauses 21-33, wherein the core holder is a first core holder, the apparatus comprising at least a second core holder disposed inside the environmental chamber.

Clause 35. A method of characterizing a fluid-solid system, the method comprising:
(a) placing a porous rock sample in a core holder;
(b) contacting the porous rock sample with a fluid to create the fluid-solid system inside the core holder;
(c) automatically adjusting a temperature and/or pressure of the fluid-solid system to a preselected value via a processor and at least one automated valve;
(d) monitoring the fluid-solid system for equilibrium;
(e) recording a value for temperature, pressure and/or mass of the fluid-solid system;
(f) performing an action based on the recorded data; and
(g) repeating operations (c) through (f) to produce a thermodynamic data characteristic of the fluid-solid system.

Clause 36. The method of Clause 35, wherein the fluid-solid system is monitored for equilibrium via a pressure sensor.

Clause 37. The method of Clause 35 or Clause 36, wherein the performing an action operation (f) comprises analyzing a pressure signal for stationarity, wherein the pressure signal corresponds to the pressure within the core holder.

Clause 38. The method of Clause 37, wherein the analyzing the pressure signal for stationarity comprises performing an Augmented Dickey-Fuller (ADF) test and/or a Kwiatkowski-Phillips-Schmidt-Shin (KPSS) test.

Clause 39. The method of any one of Clauses 35-38, wherein the at least one automated valve is a pressure control valve, and wherein the performing an action operation (f) comprises opening the pressure control valve for a calculated period of time.

Clause 40. The method of any one of Clauses 35-39, wherein the performing an action operation (f) comprises:
performing a series of short valve openings in order to generate a series of data;
analyzing the series of data in order to calculate the calculated period of time; or
a combination thereof.

Clause 41. The method of any one of Clauses 35-40, wherein the performing an action operation (f) comprises calculating an average of pressure and/or mass values over a pre-determined time duration.

Clause 42. The method of any one of Clauses 35-41, wherein the performing an action operation (f) comprises adjusting the pressure of the fluid-solid system.

Clause 43. The method of Clause 42, wherein the adjusting the pressure of the fluid-solid system comprises introducing additional fluid into the core holder.

Clause 44. The method of Clause 43, wherein the introducing additional fluid into the core holder comprises opening an automated valve for a predetermined duration of time, via the processor, wherein the automated valve is in fluid communication with a source of pressure.

Clause 45. The method of Clause 44, wherein the source of pressure comprises a vessel of compressed gas.

Clause 46. The method of Clause 43, wherein the adjusting the pressure of the fluid-solid system comprises removing at least some fluid from the core holder.

Clause 47. The method of Clause 46, wherein the removing at least some fluid from the core holder comprises opening an automated valve for a predetermined duration of time, via the processor, wherein the automated valve is in fluid communication with a source of vacuum.

Clause 48. The method of any one of Clauses 35-47, further comprising controlling the atmosphere within the environmental chamber via an automated purge valve, the automated purge valve being in selective fluid communication with a source of non-reactive gas.

Clause 49. The method of any one of Clauses 35-48, comprising automatically interpreting, transforming, and recording unprocessed signals from a pressure sensor, a temperature sensor, and a mass comparator into a thermodynamic data characteristic of the fluid-solid system.

As is apparent from the foregoing general description and the specific embodiments, while forms of the embodiments have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "Is" preceding the recitation of the composition, element, or elements and vice versa, e.g., the terms "comprising," "consisting essentially of," "consisting of" also include the product of the combinations of elements listed after the term.

As used herein, a "composition" can include component(s) of the composition and/or reaction product(s) of two or more components of the composition. Compositions of the present disclosure can be prepared by any suitable mixing process. As used herein, a "formulation" can include component(s) of the formulation and/or reaction product(s) of two or more components of the formulation. The formulation can be prepared by any suitable mixing process.

References cited herein are incorporated by reference herein in their entirety to indicate the state of the art as of their publication or filing date and it is intended that this information can be employed herein, if needed, to exclude specific embodiments that are in the prior art.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, embodiments comprising "a core holder" include embodiments comprising one, two, or more core holders, unless specified to the contrary or the context clearly indicates only one core holder is included.

While the foregoing is directed to embodiments of the present disclosure, other and further aspects of the disclosure may be devised without departing from the basic scope thereof, and the scope thereof is determined by the claims that follow.

What is claimed is:

1. An apparatus for characterizing a fluid-solid system, the apparatus comprising:
a core holder;
a pressure sensor coupled to the core holder, the pressure sensor configured to sense a pressure within the core holder and produce a pressure signal;
a mass comparator operationally connected to an interior of the core holder; and
a pressure and flow control system comprising:
a pressure source in selective fluid communication with the core holder;
an automated pressure valve configured to control pressure within the core holder; and
a processor configured to:
control the automated pressure valve based at least in part on the pressure signal;
step the pressure within the core holder through a series of predetermined pressure set points; and
log data from the pressure sensor and the mass comparator.

2. The apparatus of claim 1, wherein the processor is further configured to:
control the pressure within the core holder to a first predetermined pressure set point;
analyze the pressure signal for stationarity; and
open the automated pressure valve for a calculated period of time to control the pressure within the core holder to a second predetermined pressure set point.

3. The apparatus of claim 2, wherein the processor is further configured to analyze the pressure signal for stationarity by an Augmented Dickey-Fuller (ADF) test and/or a Kwiatkowski-Phillips-Schmidt-Shin (KPSS) test.

4. The apparatus of claim 2, wherein the processor is further configured to calculate the calculated period of time by:
performing a series of short valve openings in order to generate a series of data; and
analyzing the series of data in order to calculate the calculated period of time.

5. The apparatus of claim 1, further comprising:
a vacuum source in selective fluid communication with the core holder; and
an automated vacuum valve configured to control pressure within the core holder, wherein the processor is further configured to control the automated vacuum valve.

6. The apparatus of claim 1, wherein:
the core holder is disposed inside an environmental chamber, the environmental chamber comprising:
a heating element, a cooling element, or both; and
a temperature sensor; and
the processor is further configured to control a temperature within the environmental chamber.

7. The apparatus of claim 1, further comprising a gas chromatograph operably connected to the core holder, wherein the processor is further configured to automatically direct contents of the core holder into the gas chromatograph.

8. The apparatus of claim 1, wherein the processor is further configured to automatically log data from the pressure sensor and the mass comparator.

9. The apparatus of claim 1, wherein the core holder is a first core holder, the apparatus further comprising at least a second core holder.

10. A method of characterizing a fluid-solid system, the method comprising:
(a) contacting a porous rock sample, disposed within a core holder, with a fluid to form a fluid-solid system inside the core holder;
(b) automatically adjusting a temperature of the fluid-solid system, a pressure of the fluid-solid system, or both, to a preselected value via a processor and at least one automated valve;
(c) monitoring the fluid-solid system for equilibrium via a pressure sensor;
(d) recording a value for temperature, a value for pressure, a value for mass, or a combination thereof, of the fluid-solid system, to provide recorded data;
(e) performing an action based on the recorded data, the performing an action comprising at least:
analyzing a pressure signal for stationarity by performing an Augmented Dickey-Fuller (ADF) test, a Kwiatkowski-Phillips-Schmidt-Shin (KPSS) test, or both, the pressure signal corresponding to the pressure within the core holder; and
(f) repeating one or more of operations (b) through (e) to produce a thermodynamic data characteristic of the fluid-solid system.

11. The method of claim 10, wherein:
the at least one automated valve is a pressure control valve; and
the performing an action of operation (e) further comprises opening the pressure control valve for a calculated period of time.

12. The method of claim 11, wherein the performing an action of operation (e) further comprises:
performing a series of short valve openings in order to generate a series of data; and
analyzing the series of data in order to calculate the calculated period of time.

13. The method of claim 10, wherein the performing an action of operation (e) further comprises calculating an average of pressure values, an average of mass values, or both, over a pre-determined time duration.

14. The method of claim 10, wherein the performing an action of operation (e) further comprises adjusting the pressure of the fluid-solid system, the adjusting the pressure of the fluid-solid system comprising:
introducing additional fluid into the core holder;
removing at least some fluid from the core holder; or
a combination thereof.

15. The method of claim 14, wherein:
when the performing an action of operation (e) further comprises introducing additional fluid into the core holder, the introducing additional fluid into the core holder comprises opening an automated valve for a predetermined duration of time, via the processor, the automated valve being in fluid communication with a source of pressure; or when the performing an action of operation (e) further comprises removing at least some fluid from the core holder, the removing at least some fluid from the core holder comprises opening an automated valve for a predetermined duration of time, via the processor, the automated valve being in fluid communication with a source of vacuum.

16. The method of claim 10, wherein the core holder is disposed within an environmental chamber, and wherein the method further comprises controlling an atmosphere within the environmental chamber via an automated purge valve, the automated purge valve being in selective fluid communication with a source of non-reactive gas.

17. The method of claim 10, further comprising automatically interpreting, transforming, and recording unprocessed signals from a pressure sensor, a temperature sensor, and a mass comparator into a thermodynamic data characteristic of the fluid-solid system.

18. A method of characterizing a fluid-solid system, comprising:
   (a) introducing a fluid with a porous rock sample disposed within a core holder to form a fluid-solid system inside the core holder;
   (b) automatically adjusting a pressure of the fluid-solid system to a preselected value via a processor and at least one automated valve, wherein the automatically adjusting comprises:
      performing a series of short valve openings in order to generate a series of data; and
      analyzing the series of data in order to calculate a calculated period of time;
   (c) monitoring the fluid-solid system for equilibrium by a pressure sensor;
   (d) recording a value for pressure, a value for mass, or a combination thereof, of the fluid-solid system, to provide recorded data;
   (e) performing an action based on the recorded data, the performing an action comprising:
      analyzing a pressure signal for stationarity by performing an Augmented Dickey-Fuller (ADF) test, a Kwiatkowski-Phillips-Schmidt-Shin (KPSS) test, or both, the pressure signal corresponding to the pressure within the core holder; and
   (f) repeating one or more of operations (b) through (e) to produce thermodynamic data characteristic of the fluid-solid system.

19. The method of claim 18, wherein the core holder is disposed within an environmental chamber, and wherein the method further comprises controlling an atmosphere within the environmental chamber via an automated purge valve, the automated purge valve being in selective fluid communication with a source of non-reactive gas.

20. The method of claim 18, further comprising automatically interpreting, transforming, and recording unprocessed signals from a pressure sensor, a temperature sensor, and a mass comparator into a thermodynamic data characteristic of the fluid-solid system.

* * * * *